US009892895B2

(12) United States Patent
Dai et al.

(10) Patent No.: US 9,892,895 B2
(45) Date of Patent: Feb. 13, 2018

(54) METHOD FOR ANALYZING SMALL MOLECULE COMPONENTS OF A COMPLEX MIXTURE IN A MULTI-SAMPLE PROCESS, AND ASSOCIATED APPARATUS AND COMPUTER PROGRAM PRODUCT

(71) Applicant: METABOLON, INC., Durham, NC (US)

(72) Inventors: Hongping Dai, Chapel Hill, NC (US); Corey Donald DeHaven, Raleigh, NC (US)

(73) Assignee: METABOLON, INC., Durham, NC (US)

( * ) Notice: Subject to any disclaimer, the term of this patent is extended or adjusted under 35 U.S.C. 154(b) by 0 days.

(21) Appl. No.: 15/315,147

(22) PCT Filed: May 28, 2015

(86) PCT No.: PCT/US2015/032803
§ 371 (c)(1),
(2) Date: Nov. 30, 2016

(87) PCT Pub. No.: WO2015/184048
PCT Pub. Date: Dec. 3, 2015

(65) Prior Publication Data
US 2017/0117122 A1   Apr. 27, 2017

Related U.S. Application Data

(60) Provisional application No. 62/005,596, filed on May 30, 2014.

(51) Int. Cl.
*G01N 30/86* (2006.01)
*H01J 49/02* (2006.01)
(Continued)

(52) U.S. Cl.
CPC ...... *H01J 49/0036* (2013.01); *G01N 30/8634* (2013.01); *G01N 30/8644* (2013.01); *G01N 33/6848* (2013.01); *H01J 49/04* (2013.01)

(58) Field of Classification Search
CPC . H01J 49/0036; G01N 30/72; G01N 30/8624; G01N 30/8631; G01N 30/8634; G01N 30/8651; G01N 30/8675
(Continued)

(56) References Cited

U.S. PATENT DOCUMENTS 5,672,869 A  *  9/1997  Windig  ............... H01J 49/0036
                                                          250/282
6,873,915 B2 *  3/2005  Hastings  ............ G01N 30/8624
                                                          250/282
(Continued)

*Primary Examiner* — David A Vanore
(74) *Attorney, Agent, or Firm* — Womble Bond Dickinson (US) LLP

(57) ABSTRACT

A method, apparatus, and computer-readable storage medium for analyzing sample data from a component separation/mass spectrometer system. A profile plot is formed for each sample, each having retention time and intensity axes, the intensity being represented as a function of retention time for a selected sample ion mass. An intensity peak arrangement, including at least one identifying peak, each having a peak range and characteristic intensity, is identified for a selected ion in the profile plot for each sample. An orthogonal plot, corresponding to the profile plot, for each sample is formed, extending along the retention time axis perpendicularly to the intensity axis. The characteristic intensity of each of the at least one identifying peak is represented on the retention time axis of the orthogonal plot with gradated indicia.

45 Claims, 11 Drawing Sheets

(51) Int. Cl.
*G06F 17/18* (2006.01)
*H01J 49/00* (2006.01)
*G01N 33/68* (2006.01)
*H01J 49/04* (2006.01)

(58) Field of Classification Search
USPC .......... 250/282, 281; 702/22, 19, 23, 27, 32; 703/11, 12
See application file for complete search history.

(56) References Cited

U.S. PATENT DOCUMENTS

| | | | |
|---|---|---|---|
| 7,381,944 B2 * | 6/2008 | Cameron | G01N 27/624 250/282 |
| 7,884,318 B2 * | 2/2011 | Milgram | G01N 30/8651 250/281 |
| 8,428,881 B2 * | 4/2013 | Winfield | G06F 19/24 702/19 |
| 2001/0037178 A1 * | 11/2001 | Bush | G01V 1/30 702/14 |
| 2004/0181345 A1 * | 9/2004 | Kolossov | G06F 19/707 702/22 |
| 2015/0162175 A1 * | 6/2015 | Wright | G01N 30/8682 250/282 |

* cited by examiner

METHOD FOR ANALYZING SMALL MOLECULE COMPONENTS OF A COMPLEX MIXTURE IN A MULTI-SAMPLE PROCESS, AND ASSOCIATED APPARATUS AND COMPUTER PROGRAM PRODUCT

CROSS-REFERENCE TO RELATED APPLICATIONS

This application is a national stage filing under 35 U.S.C. 371 of International Application No. PCT/US2015/032803, filed May 28, 2015, which International Application was published by the International Bureau in English on Dec. 3, 2015, and claims priority to U.S. Provisional Application No. 62/005,596, filed May 30, 2016. The disclosures of each of the applications noted above are incorporated herein by reference in their entirety.

BACKGROUND OF THE DISCLOSURE

Field of the Disclosure

The present disclosure relates to the field of analyzing small molecule components in a complex mixture and, more particularly, to a method and associated apparatus and computer program product for analyzing small molecule components of a complex mixture in a multi-sample process, with such small molecule analysis including metabolomics, which is the study of small molecules produced by an organism's metabolic processes, or other analysis of small molecules produced through metabolism.

Description of Related Art

Metabolomics is the study of the small molecules, or metabolites, contained in a cell, tissue or organ (including fluids) and involved in primary and intermediary metabolism. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds or other therapy.

Molecular biology techniques for uncovering the biochemical processes underlying disease have been centered on the genome, which consists of the genes that make up DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites and their role in metabolism may be readily identified. In this context, the identification of disease targets may be expedited with greater accuracy relative to other known methods. The collection of metabolomic data for use in identifying disease pathways is generally known in the art, as described generally, for example, in U.S. Pat. Nos. 7,005,255 and 7,329,489 to Metabolon, Inc., each entitled Methods for Drug Discovery, Disease Treatment, and Diagnosis Using Metabolomics. Additional uses for metabolomics data are described therein and include, for example, determining response to a therapeutic agent (i.e., a drug) or other xenobiotics, monitoring drug response, determining drug safety, and drug discovery. However, the collection and sorting of metabolomic data taken from a variety of samples (e.g., from a patient population) consumes large amounts of time and computational power. For example, according to some known metabolomic techniques, spectrometry data for certain samples is collected and plotted in three (or more) dimensions (i.e., sample properties that can be represented along an axis with respect to other sample properties) and stored in an individual file corresponding to each sample. This data is then, by individual file, compared to data corresponding to a plurality of known metabolites in order to identify known metabolites that may be disease targets. The data may also be used for identification of toxic agents and/or drug metabolites. Furthermore such data may also be used to monitor the effects of xenobiotics and/or used to monitor/measure/identify the xenobiotics and associated metabolites produced by processing (metabolizing) the xenobiotics. However, such conventional "file-based" methods (referring to the individual data file generated for each sample) require the use of large amounts of computing power and memory capacity to handle the screening of large numbers of known metabolites. Furthermore, "file-based" data handling may not lend itself to the compilation of sample population data across a number of samples because, according to known metabolomic data handling techniques, each sample is analyzed independently, without taking into account subtle changes in metabolite composition that may be more readily detectable across a sample population. Furthermore, existing "file-based" method may have other limitations including: limited security and auditability; and poor data set consistency across multiple file copies. In addition, individual files may not support multiple indices (i.e., day collected, sample ID, control vs. treated, drug dose, etc.) such that all files must be scanned when only a particular subset is desired.

These limitations in current metabolomic data analysis techniques may lead to the discarding of potentially relevant and/or valuable metabolomic data that may be used to identify and classify particular metabolites as disease targets. Specifically, spectrometry data corresponding to a number of samples (such as tissue samples from individual human subjects) generally results in a large data file corresponding to each sample, wherein each data file must then be subjected to an individual screening process with respect to a library of known metabolites. However, conventional systems do not readily allow for the consolidation of spectrometry data from a number of samples for the subjective evaluation of the data generated by the spectrometry processes. Thus, while a single file corresponding to an individual sample may be inconclusive, such data may be more telling if viewed subjectively in a succinct format with respect to other samples within a sample population.

One particular example of a limitation in current metabolomic data analysis techniques involves the identification and quantification of a metabolite in each of a plurality of sample. In some instances, the identification of the metabolite involves analyzing the data file of each sample to determine whether an indication (i.e., an intensity peak for a particular sample ion mass or sample component mass, observed at a particular retention time or range or retention times) of that metabolite exists within the respective data files. If such an indication is determined, quantification of that metabolite may then involve the integration (mathematical calculation of area) of the area represented by that indication (i.e., the area under the intensity peak). However, as previously noted, it may be difficult in "file based" data handling methods to verify whether the determined indication is consistent across samples. For example, it may be difficult to determine whether the identified intensity peaks are aligned with respect to retention time across the samples. Further, there may be instances where the indication (i.e., the intensity peak) is not clearly defined within the data file of one or more samples. In those instances, the integration procedure used to calculate the area represented by the indication may vary, for instance, based on the assumptions used or estimates performed in connection with the calculation, particularly where the origin and the terminus of a particular intensity peak is not clearly evident. There may also be instances where the indication (i.e., the intensity peak) may actually reflect the presence of more than one sample component and, as such, any analysis of those intensity peaks as a whole may be significantly inaccurate. As such, the various assumptions and estimates, which may be difficult to analyze for individual samples when using a file-base data handling method, may result in an inaccurate indication of the quantity of that metabolite (or a plurality of metabolites) present over the plurality of the sample. In this regard, such a quantitative inaccuracy introduced into a metabolomics analysis at such an early stage may lead to larger inaccuracies in subsequent steps or analyses.

Therefore, there exists a need for an improved apparatus and method for solving the technical issues outlined above that are associated with conventional metabolomic data analysis systems. More particularly, there exists a need for an apparatus and method capable of analyzing spectrometry data across samples, with the option of, but not the need for, generating a separate data file for each sample. There also exists a need for an apparatus and method capable of allowing a user to subjectively evaluate spectrometry data across a plurality of samples to identify selected metabolites, for allowing the user to verify or otherwise determine the confidence in the identification of the selected metabolites, for allowing the user to examine the data associated with the identification of the selected metabolites, for example, for sorting, grouping, and/or aligning purposes, and for allowing the user to determine additional information related to the identified selected metabolites, for instance, for quality control and consistency verification purposes. There also exists a need for an improved apparatus and method capable of more accurately identifying and quantifying sample components across samples from the acquired spectrometry data.

BRIEF SUMMARY OF THE DISCLOSURE

The above and other needs are met by aspects of the present disclosure which, in one aspect, provides a method of analyzing data for a plurality of samples obtained from a component separation and mass spectrometer system, wherein the data includes a data set for each sample, and wherein each data set includes a sample indicia (i.e., a sample identifier such as, e.g., a number, a name, an ID, or other suitable/unique designation or combinations thereof), a sample ion mass or sample component mass, a retention time, and an intensity. Such a method may comprise forming a profile plot for each sample from the data obtained from the component separation and mass spectrometer system and corresponding to the respective sample, with each profile plot having a retention time axis and an intensity axis, and including a graphical representation of intensity as a function of retention time for a selected sample ion mass. An intensity peak arrangement corresponding to a selected ion is identified in the profile plot for each sample, with the intensity peak arrangement including at least one identifying peak, and with each of the at least one identifying peak having a peak range and a characteristic intensity within the peak range. An orthogonal plot, corresponding to the profile plot, is formed for each sample, with the orthogonal plot extending along the retention time axis in a plane perpendicular to the intensity axis. The characteristic intensity of each of the at least one identifying peak is represented on the retention time axis of the orthogonal plot with gradated indicia. In some aspects, the at least one identifying peak includes a main peak and at least one sub-peak, such that the characteristic intensity of each of the at least one identifying peak is represented on the retention time axis of the orthogonal plot with gradated indicia having a maximum expression for the characteristic intensity of the main peak and a lesser expression for the characteristic intensity of each of the at least one sub-peak. In some instances, the peak range of each of the at least one identifying peak is represented on the orthogonal plot with range indicia, with the range indicia having a first indicium representing an initiation of the peak range and a second indicium representing a termination of the peak range, for the main peak and each of the at least one sub-peak.

Another aspect of the present disclosure provides an apparatus for analyzing data for a plurality of samples obtained from a component separation and mass spectrometer system, with the data including a data set for each sample, and with each data set including a sample indicia, a sample ion mass, a retention time, and an intensity, wherein the apparatus comprises a processor and a memory storing executable instructions that, in response to execution by the processor, cause the apparatus to at least perform the steps of the method aspect of the present disclosure.

A further aspect of the present disclosure provides a computer program product for analyzing data for a plurality of samples obtained from a component separation and mass spectrometer system, with the data including a data set for each sample, and with each data set including a sample indicia, a sample ion mass, a retention time, and an intensity, wherein the computer program product comprises at least one non-transitory computer readable storage medium having computer-readable program code stored thereon, the computer-readable program code comprising program code that is executable to at least perform the steps of the method aspect of the present disclosure.

The present disclosure thus includes, without limitation, the following embodiments:

Embodiment 1

A method of analyzing data for a plurality of samples obtained from a component separation and mass spectrometer system, the data including a data set for each sample, each data set including sample indicia, sample ion mass, retention time, and intensity, wherein such a method comprises forming a profile plot for each sample from the data obtained from the component separation and mass spectrometer system and corresponding to the respective sample, wherein each profile plot has a retention time axis and an intensity axis, and includes a graphical representation of intensity as a function of retention time for a selected sample ion mass; identifying an intensity peak arrangement corresponding to a selected ion in the profile plot for each sample, wherein the intensity peak arrangement includes at least one identifying peak, and wherein each of the at least one identifying peak has a peak range and a characteristic intensity within the peak range; forming an orthogonal plot, corresponding to the profile plot, for each sample, wherein the orthogonal plot extends along the retention time axis in a plane perpendicular to the intensity axis; and representing the characteristic intensity of each of the at least one identifying peak on the retention time axis of the orthogonal plot with gradated indicia.

Embodiment 2

The method of any preceding or subsequent embodiment, or combinations thereof, wherein representing the characteristic intensity of each of the at least one identifying peak further comprises representing the characteristic intensity of the at least one identifying peak on the retention time axis of the orthogonal plot with gradated indicia having an expression for each of the at least one identifying peak in proportion to a relation of the characteristic intensity to a defined range.

Embodiment 3

The method of any preceding or subsequent embodiment, or combinations thereof, wherein the at least one identifying peak includes a main peak and at least one sub-peak, and wherein representing the characteristic intensity of each of the at least one identifying peak further comprises representing the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

Embodiment 4

The method of any preceding or subsequent embodiment, or combinations thereof, further comprising representing the peak range of each of the at least one identifying peak on the orthogonal plot with range indicia, wherein the range indicia has a first indicium representing an initiation of the peak range and a second indicium representing a termination of the peak range, for each of the at least identifying peak.

Embodiment 5

The method of any preceding or subsequent embodiment, or combinations thereof, wherein the at least one identifying peak includes a main peak and at least one sub-peak, wherein representing the peak range of each of the at least one identifying peak on the orthogonal plot with range indicia, comprises representing the peak range of each of the at least one identifying peak on the orthogonal plot with range indicia, with the second indicium of the range indicia of the main peak also representing the first indicium of the range indicia of a next sub-peak of the intensity peak arrangement, and wherein the next sub-peak is one of a shoulder peak and a secondary peak associated with the main peak.

Embodiment 6

The method of any preceding or subsequent embodiment, or combinations thereof, wherein the at least one identifying peak includes a main peak and at least one sub-peak, wherein representing the peak range of each of the at least one identifying peak on the orthogonal plot with range indicia, comprises representing the peak range of each of the at least one identifying peak on the orthogonal plot with range indicia, with the second indicium of the range indicia of one of the sub-peaks also representing the first indicium of the range indicia of a next sub-peak of the intensity peak arrangement, and wherein the next sub-peak is one of a shoulder peak and a secondary peak associated with the one of the sub-peaks.

Embodiment 7

The method of any preceding or subsequent embodiment, or combinations thereof, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

Embodiment 8

The method of any preceding or subsequent embodiment, or combinations thereof, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

Embodiment 9

The method of any preceding or subsequent embodiment, or combinations thereof, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

Embodiment 10

The method of any preceding or subsequent embodiment, or combinations thereof, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with different shapes, including a first shape for the characteristic intensity of the main peak and a second shape for the characteristic intensity of one of the at least one sub-peak.

Embodiment 11

The method of any preceding or subsequent embodiment, or combinations thereof, further comprising forming a first across-sample plot from the orthogonal plots of the plurality of samples, wherein the first across-sample plot has the retention time axis and a sample indicia axis, and includes a graphical representation of the orthogonal plots across the plurality of samples.

Embodiment 12

The method of any preceding or subsequent embodiment, or combinations thereof, further comprising determining an area associated with any of the at least one identifying peak of the intensity peak arrangement for the selected ion, using an integration procedure, wherein the determined area is associated with a relative quantity of an ion component corresponding thereto in the respective sample.

Embodiment 13

The method of any preceding or subsequent embodiment, or combinations thereof, further comprising determining an identity peak for the selected ion from the at least one identifying peak, wherein determining an area comprises determining an area associated with the identity peak for the selected ion, using an integration procedure, and wherein the determined area of the identity peak is associated with a relative quantity of the selected ion corresponding thereto in the respective sample.

Embodiment 14

The method of any preceding or subsequent embodiment, or combinations thereof, further comprising selectively toggling between the profile plot and the orthogonal plot of the intensity peak arrangement of at least one of the samples.

Embodiment 15

The method of any preceding or subsequent embodiment, or combinations thereof, further comprising concurrently displaying the profile plot and the orthogonal plot of the ion peak arrangement of at least one of the samples.

Embodiment 16

The method of any preceding or subsequent embodiment, or combinations thereof, further comprising superimposing the profile plots of the selected ion for at least a portion of the samples on a second across-sample plot.

Embodiment 17

The method of any preceding or subsequent embodiment, or combinations thereof, further comprising forming a first across-sample plot from the orthogonal plots of the plurality of samples, wherein the first across-sample plot has the retention time axis and a sample indicia axis, and includes a graphical representation of the orthogonal plots across the plurality of samples, and displaying the second across-sample plot concurrently with the first across-sample plot.

Embodiment 18

An apparatus for analyzing data for a plurality of samples obtained from a component separation and mass spectrometer system, the data including a data set for each sample, each data set including sample indicia, sample ion mass, retention time, and intensity, wherein the apparatus comprising a processor and a memory storing executable instructions that, in response to execution by the processor, cause the apparatus to at least perform the steps of forming a profile plot for each sample from the data obtained from the component separation and mass spectrometer system and corresponding to the respective sample, wherein each profile plot having a retention time axis and an intensity axis, and includes a graphical representation of intensity as a function of retention time for a selected sample ion mass; identifying an intensity peak arrangement corresponding to a selected ion in the profile plot for each sample, wherein the intensity peak arrangement includes at least one identifying peak, and wherein each of the at least one identifying peak has a peak range and a characteristic intensity within the peak range; forming an orthogonal plot, corresponding to the profile plot, for each sample, wherein the orthogonal plot extends along the retention time axis in a plane perpendicular to the intensity axis, and is displayed on a display; and representing the characteristic intensity of each of the at least one identifying peak on the retention time axis of the orthogonal plot with gradated indicia.

Embodiment 19

The apparatus of any preceding or subsequent embodiment, or combinations thereof, wherein the memory stores executable instructions that, in response to execution by the processor, cause the apparatus to further perform the step of representing the characteristic intensity of the at least one identifying peak on the retention time axis of the orthogonal plot with gradated indicia having an expression for each of the at least one identifying peak in proportion to a relation of the characteristic intensity to a defined range.

Embodiment 20

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

Embodiment 21

The apparatus of any preceding or subsequent embodiment, or combinations thereof, wherein the memory stores executable instructions that, in response to execution by the processor, cause the apparatus to further perform the step of representing the peak range of each of the at least one identifying peak on the orthogonal plot with range indicia, wherein the range indicia has a first indicium representing an initiation of the peak range and a second indicium representing a termination of the peak range, for each of the at least one identifying peak.

Embodiment 22

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the peak range of each of the at least one identifying peak on the orthogonal plot with range indicia, with the second indicium of the range indicia of the main peak also representing the first indicium of the range indicia of a next sub-peak of the intensity peak arrangement, wherein the next sub-peak is one of a shoulder peak and a secondary peak associated with the main peak.

Embodiment 23

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the peak range of each of the at least one identifying peak on the orthogonal plot with range indicia, with the second indicium of the range indicia of one of the sub-peaks also representing the first indicium of the range indicia of a next sub-peak of the intensity peak arrangement, wherein the next sub-peak is one of a shoulder peak and a secondary peak associated with the one of the sub-peaks.

Embodiment 24

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

Embodiment 25

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

Embodiment 26

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

Embodiment 27

The apparatus of any preceding or subsequent embodiment, or combinations thereof, wherein the at least one identifying peak includes a main peak and at least one sub-peak, and wherein the memory stores executable instructions that, in response to execution by the processor, cause the apparatus to further perform the step of representing the characteristic intensity of each of the at least one identifying peak on the retention time axis of the orthogonal plot with different shapes, including a first shape for the characteristic intensity of the main peak and a second shape for the characteristic intensity of one of the at least one sub-peak.

Embodiment 28

The apparatus of any preceding or subsequent embodiment, or combinations thereof, wherein the memory stores executable instructions that, in response to execution by the processor, cause the apparatus to further perform the step of forming a first across-sample plot from the orthogonal plots of the plurality of samples, wherein the first across-sample plot has the retention time axis and a sample indicia axis, and includes a graphical representation of the orthogonal plots across the plurality of samples displayed on the display.

Embodiment 29

The apparatus of any preceding or subsequent embodiment, or combinations thereof, wherein the memory stores executable instructions that, in response to execution by the processor, cause the apparatus to further perform the step of determining an area associated with any of the at least one identifying peak of the intensity peak arrangement for the selected ion, using an integration procedure, wherein the determined area is associated with a relative quantity of an ion component corresponding thereto in the respective sample.

Embodiment 30

The apparatus of any preceding or subsequent embodiment, or combinations thereof, wherein the memory stores executable instructions that, in response to execution by the processor, cause the apparatus to further perform the step of determining an identity peak for the selected ion from the at least one identifying peak, wherein determining an area comprises determining an area associated with the identity peak for the selected ion, using an integration procedure, and wherein the determined area of the identity peak is associated with a relative quantity of the selected ion corresponding thereto in the respective sample.

Embodiment 31

The apparatus of any preceding or subsequent embodiment, or combinations thereof, wherein the memory stores executable instructions that, in response to execution by the processor, cause the apparatus to further perform the step of selectively toggling between the profile plot and the orthogonal plot of the intensity peak arrangement of at least one of the samples displayed on the display.

Embodiment 32

The apparatus of any preceding or subsequent embodiment, or combinations thereof, wherein the memory stores executable instructions that, in response to execution by the processor, cause the apparatus to further perform the step of concurrently displaying the profile plot and the orthogonal plot of the ion peak arrangement of at least one of the samples displayed on the display.

Embodiment 33

The apparatus of any preceding or subsequent embodiment, or combinations thereof, wherein the memory stores executable instructions that, in response to execution by the processor, cause the apparatus to further perform the step of superimposing the profile plots of the selected ion for at least a portion of the samples on a second across-sample plot displayed on the display.

Embodiment 34

The apparatus of any preceding or subsequent embodiment, or combinations thereof, wherein the memory stores executable instructions that, in response to execution by the processor, cause the apparatus to further perform the step of forming a first across-sample plot from the orthogonal plots of the plurality of samples, wherein the first across-sample plot has the retention time axis and a sample indicia axis, and includes a graphical representation of the orthogonal plots across the plurality of samples displayed on the display, and displaying the second across-sample plot concurrently with the first across-sample plot on the display.

Embodiment 35

A computer program product for analyzing data for a plurality of samples obtained from a component separation and mass spectrometer system, wherein the data includes a data set for each sample, wherein each data set includes sample indicia, sample ion mass, retention time, and intensity, wherein the computer program product comprises at least one non-transitory computer readable storage medium having computer-readable program code stored thereon, and wherein the computer-readable program code comprises program code for forming a profile plot for each sample from the data obtained from the component separation and mass spectrometer system and corresponding to the respective sample, wherein each profile plot has a retention time axis and an intensity axis, and includes a graphical representation of intensity as a function of retention time for a selected sample ion mass; program code for identifying an intensity peak arrangement corresponding to a selected ion in the profile plot for each sample, wherein the intensity peak arrangement includes at least one identifying peak, and wherein each of the at least one identifying peak has a peak range and a characteristic intensity within the peak range; program code for forming an orthogonal plot, corresponding to the profile plot, for each sample, and directing the orthogonal plot to be displayed on a display, wherein the orthogonal plot extends along the retention time axis in a plane perpendicular to the intensity axis; and program code for representing the characteristic intensity of each of the at least one identifying peak on the retention time axis of the orthogonal plot with gradated indicia.

Embodiment 36

The computer program product of any preceding or subsequent embodiment, or combinations thereof, wherein the computer program product further comprises program code for representing the characteristic intensity of the at least one identifying peak on the retention time axis of the orthogonal plot with gradated indicia having an expression for each of the at least one identifying peak in proportion to a relation of the characteristic intensity to a defined range.

Embodiment 37

The computer program product of any preceding or subsequent embodiment, or combinations thereof, wherein the at least one identifying peak includes a main peak and at least one sub-peak, and wherein the computer program product comprises program code for representing the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

Embodiment 38

The computer program product of any preceding or subsequent embodiment, or combinations thereof, further comprising program code for representing the peak range of each of the at least one identifying peak on the orthogonal plot with range indicia, wherein the range indicia has a first indicium representing an initiation of the peak range and a second indicium representing a termination of the peak range, for each of the at least one identifying peak.

Embodiment 39

The computer program product of any preceding or subsequent embodiment, or combinations thereof, wherein the at least one identifying peak includes a main peak and at least one sub-peak, and wherein the program code for representing the peak range of each of the at least one identifying peak on the orthogonal plot with range indicia, comprises program code for representing the peak range of each of the at least one identifying peak on the orthogonal plot with range indicia, with the second indicium of the range indicia of the main peak also representing the first indicium of the range indicia of a next sub-peak of the intensity peak arrangement, wherein the next sub-peak is one of a shoulder peak and a secondary peak associated with the main peak.

Embodiment 40

The computer program product of any preceding or subsequent embodiment, or combinations thereof, wherein the at least one identifying peak includes a main peak and at least one sub-peak, and wherein the program code for representing the peak range of each of the at least one identifying peak on the orthogonal plot with range indicia, comprises program code for representing the peak range of each of the at least one identifying peak on the orthogonal plot with range indicia, with the second indicium of the range indicia of one of the sub-peaks also representing the first indicium of the range indicia of a next sub-peak of the intensity peak arrangement, wherein the next sub-peak is one of a shoulder peak and a secondary peak associated with the one of the sub-peaks.

Embodiment 41

The computer program product of any preceding or subsequent embodiment, or combinations thereof, wherein the at least one identifying peak includes a main peak and at least one sub-peak, and wherein the program code for representing the characteristic intensity of each of the at least one identifying peak on the retention time axis of the orthogonal plot, comprises program code for representing the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

Embodiment 42

The computer program product of any preceding or subsequent embodiment, or combinations thereof, wherein the program code for representing the characteristic intensity of each of the at least one identifying peak on the retention time axis of the orthogonal plot, comprises program code for representing the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

Embodiment 43

The computer program product of any preceding or subsequent embodiment, or combinations thereof, wherein the program code for representing the characteristic intensity of each of the at least one identifying peak on the retention time axis of the orthogonal plot, comprises program code for representing the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

Embodiment 44

The computer program product of any preceding or subsequent embodiment, or combinations thereof, wherein the program code for representing the characteristic intensity of each of the at least one identifying peak on the retention time axis of the orthogonal plot, comprises program code for representing the characteristic intensity of each of the at least one identifying peak on the retention time axis of the orthogonal plot with different shapes, including a first shape for the characteristic intensity of the main peak and a second shape for the characteristic intensity of one of the at least one sub-peak.

Embodiment 45

The computer program product of any preceding or subsequent embodiment, or combinations thereof, further comprising program code for forming a first across-sample plot from the orthogonal plots of the plurality of samples and displaying the first across-sample plot on the display, wherein the first across-sample plot has the retention time axis and a sample indicia axis, and includes a graphical representation of the orthogonal plots across the plurality of samples.

Embodiment 46

The computer program product of any preceding or subsequent embodiment, or combinations thereof, further comprising program code for determining an area associated with any of the at least one identifying peak of the intensity peak arrangement for the selected ion, using an integration procedure, wherein the determined area is associated with a relative quantity of an ion component corresponding thereto in the respective sample.

Embodiment 47

The computer program product of any preceding or subsequent embodiment, or combinations thereof, further comprising program code for determining an identity peak for the selected ion from the at least one identifying peak, wherein the program code for determining an area comprises program code for determining an area associated with the identity peak for the selected ion, using an integration procedure, wherein the determined area of the identity peak is associated with a relative quantity of the selected ion corresponding thereto in the respective sample.

Embodiment 48

The computer program product of any preceding or subsequent embodiment, or combinations thereof, further comprising program code for selectively toggling between the profile plot and the orthogonal plot of the intensity peak arrangement of at least one of the samples displayed on the display.

Embodiment 49

The computer program product of any preceding or subsequent embodiment, or combinations thereof, further comprising program code for concurrently displaying the profile plot and the orthogonal plot of the ion peak arrangement of at least one of the samples displayed on the display.

Embodiment 50

The computer program product of any preceding or subsequent embodiment, or combinations thereof, further comprising program code for superimposing the profile plots of the selected ion for at least a portion of the samples on a second across-sample plot displayed on the display.

Embodiment 51

The computer program product of any preceding or subsequent embodiment, or combinations thereof, further comprising program code for forming a first across-sample plot from the orthogonal plots of the plurality of samples and displaying the first across-sample plot on the display, wherein the first across-sample plot has the retention time axis and a sample indicia axis, and includes a graphical representation of the orthogonal plots across the plurality of samples, and program code for displaying the second across-sample plot concurrently with the first across-sample plot on the display.

These and other features, aspects, and advantages of the present disclosure will be apparent from a reading of the following detailed description together with the accompanying drawings, which are briefly described below. The present disclosure includes any combination of two, three, four, or more of the above-noted aspects as well as combinations of any two, three, four, or more features or elements set forth in this disclosure, regardless of whether such features or elements are expressly combined in a specific embodiment description herein. This disclosure is intended to be read holistically such that any separable features or elements of the present disclosure, in any of its various aspects and embodiments, should be viewed as intended to be combinable unless the context clearly dictates otherwise.

Thus, the apparatuses, methods, and computer program products for analyzing data obtained from a component separation and mass spectrometer system according to aspects of the present disclosure provide these and other advantages, as detailed further herein. Importantly, these advantages include a compact format that spans an "additional dimension" of the sample data, or otherwise facilitates analysis of sample data across a population of samples or between samples within the population, thereby providing increased quality and consistency of analysis results. These advantages also include the capability of identifying additional sample components and/or ion components thereof, and the improved capability of determining the relative quantity of one or more of such sample components and/or ion components thereof indicated by the recited intensity peaks or intensity peak arrangements.

BRIEF DESCRIPTION OF THE SEVERAL VIEWS OF THE DRAWINGS

Figure 1:
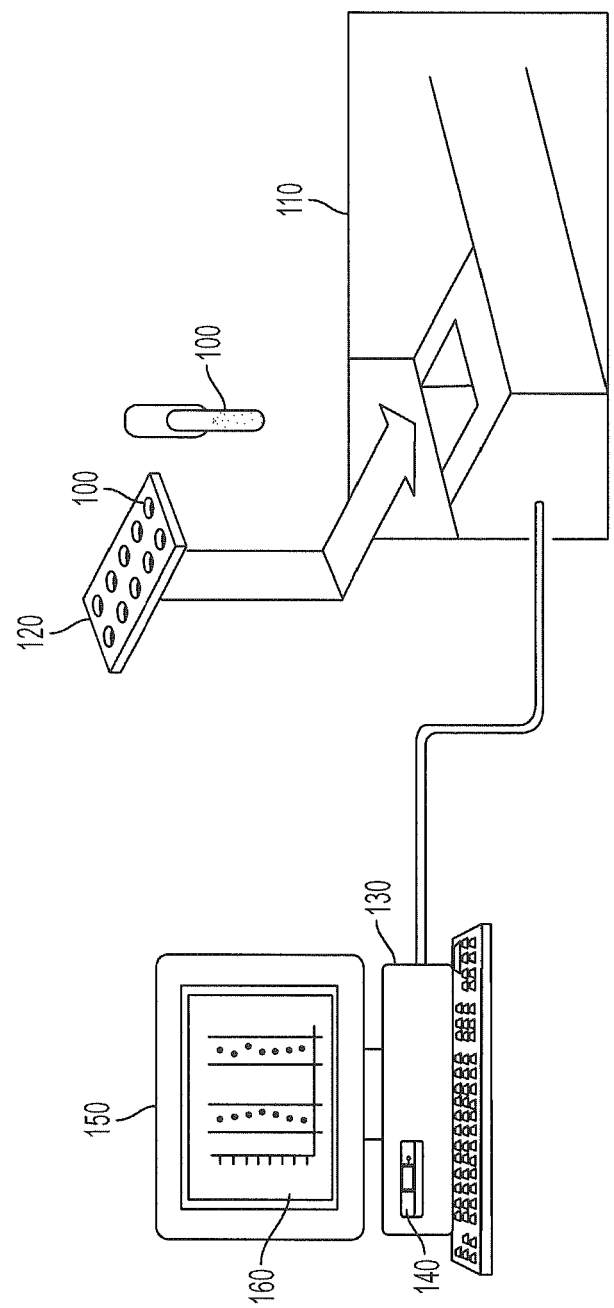
Figure 2:
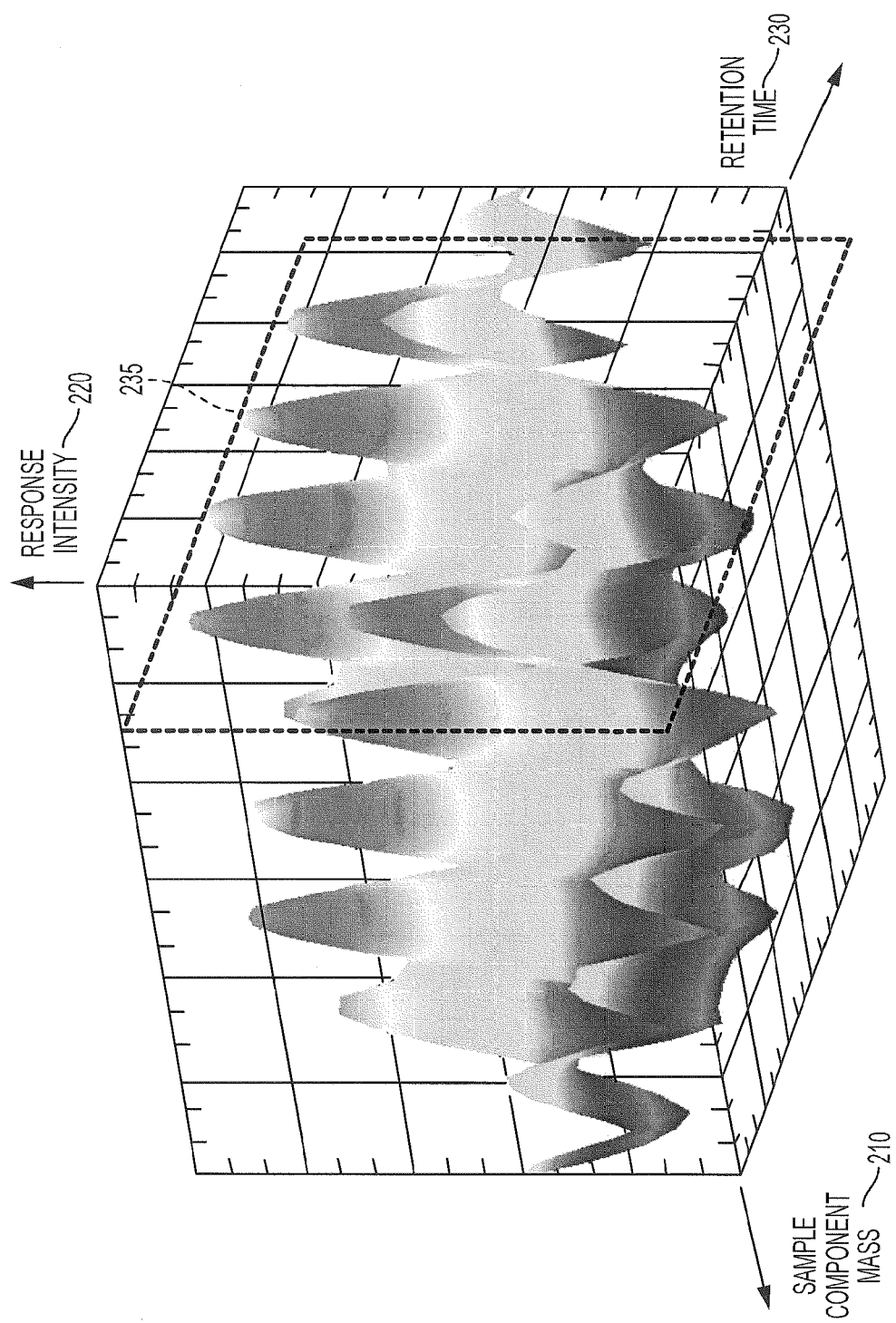
Figure 3:
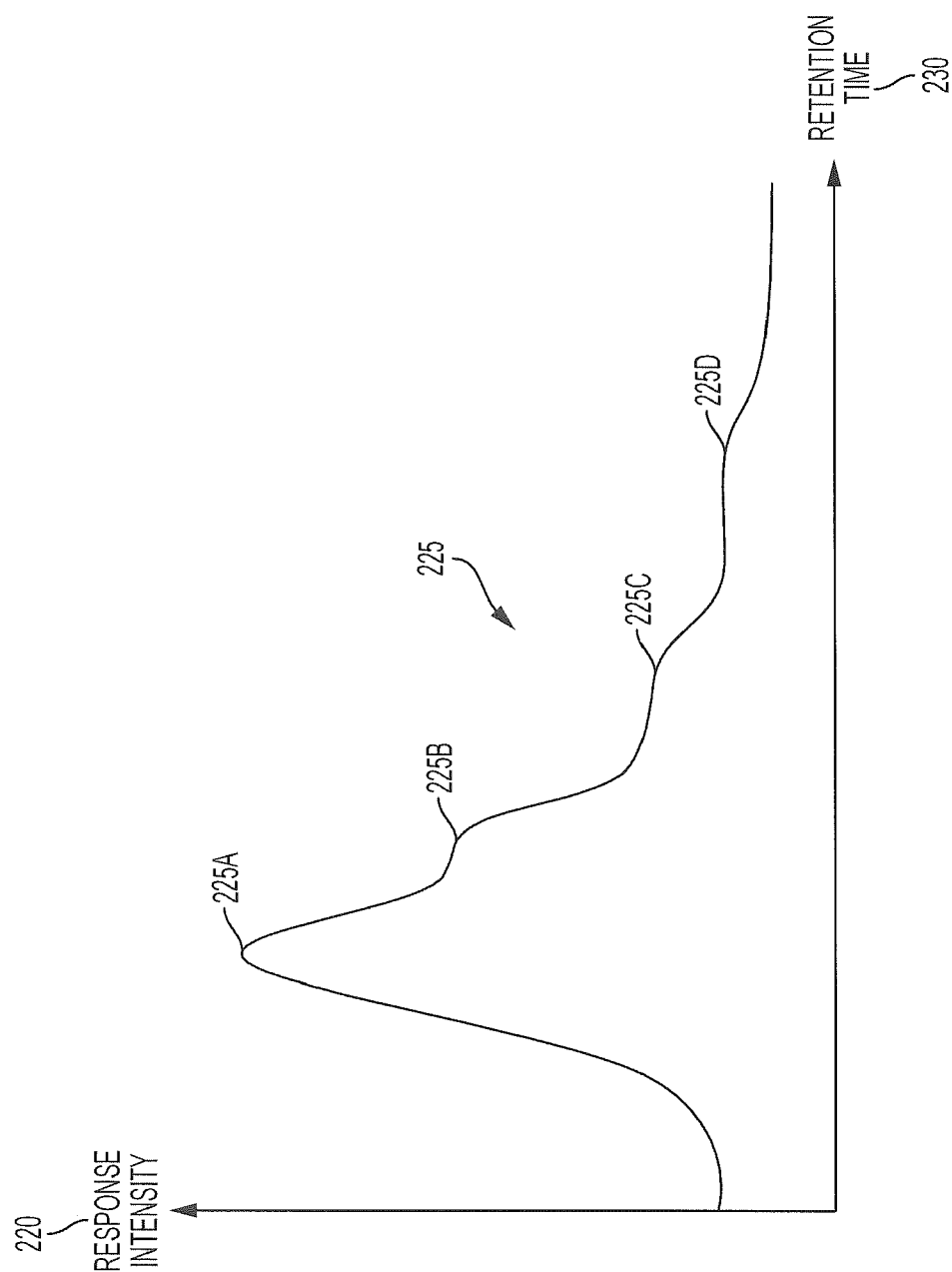
Figure 4:
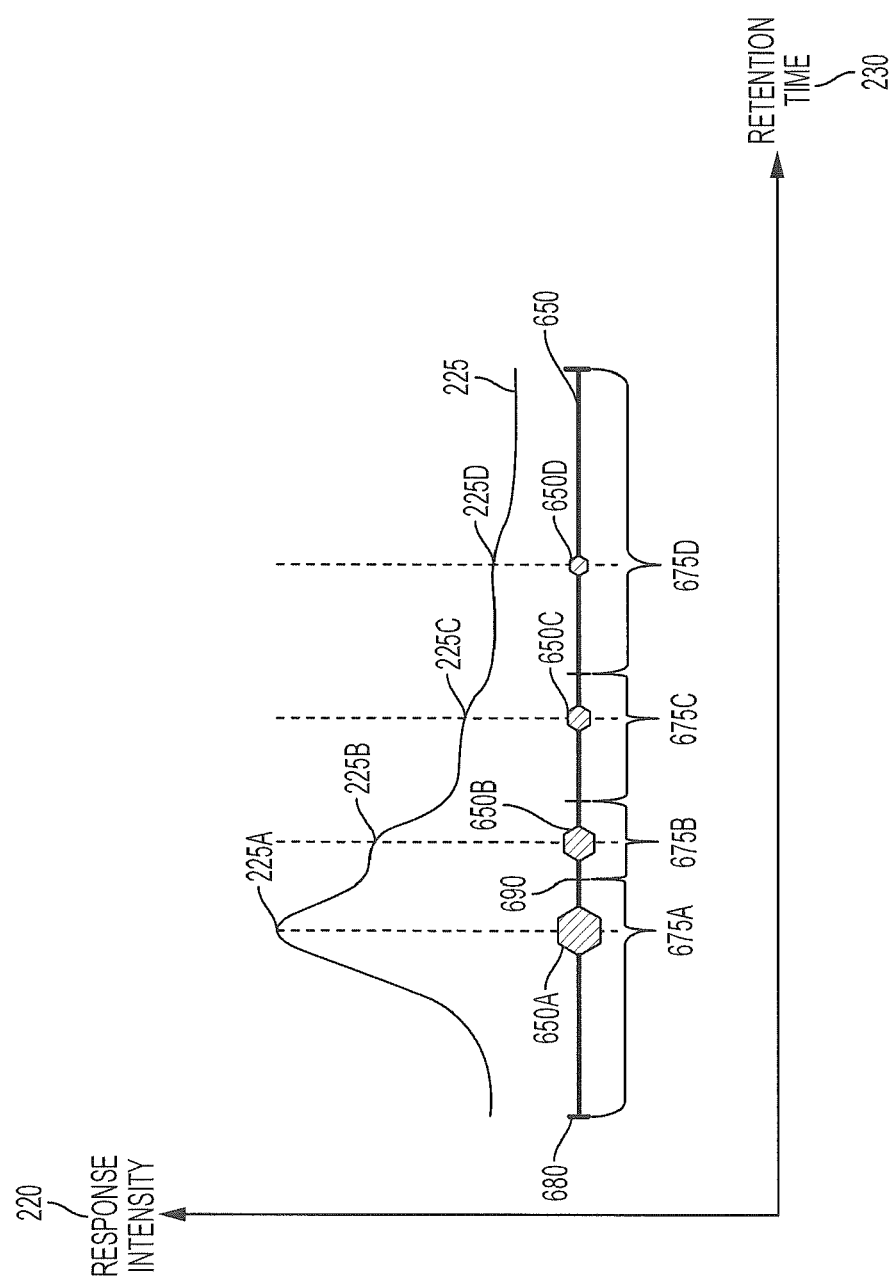
Figure 5:
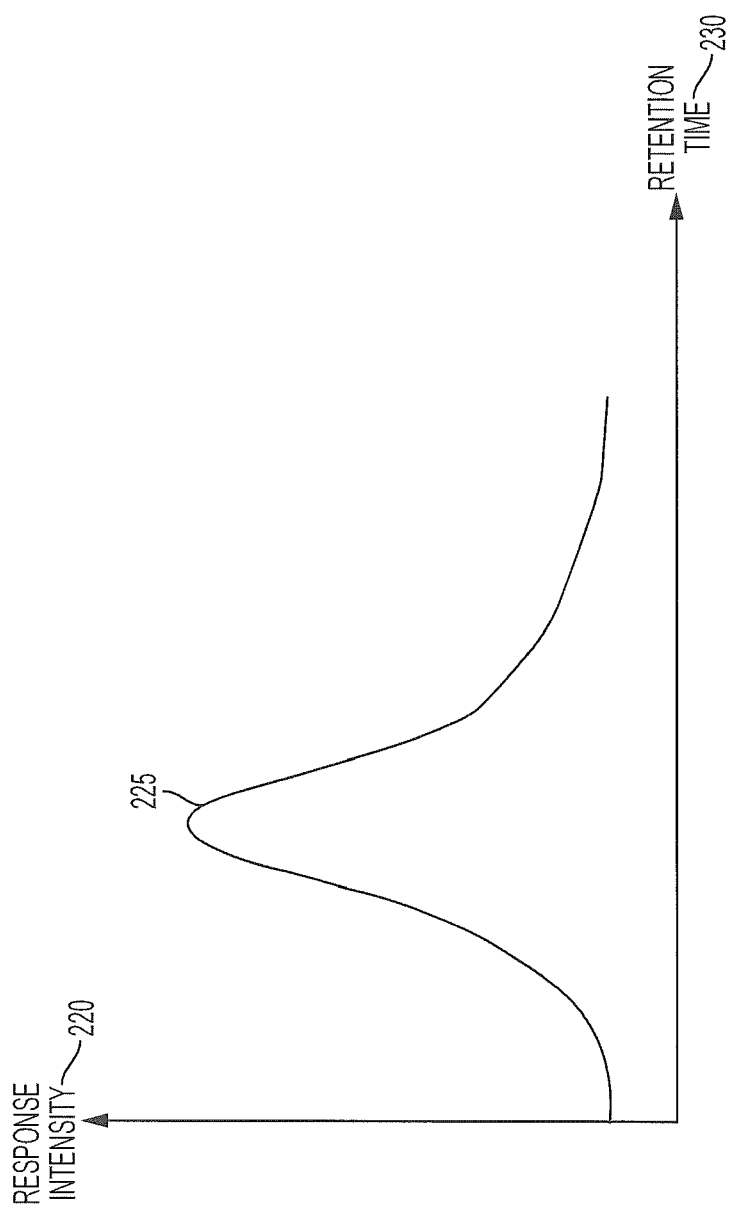
Figure 6:
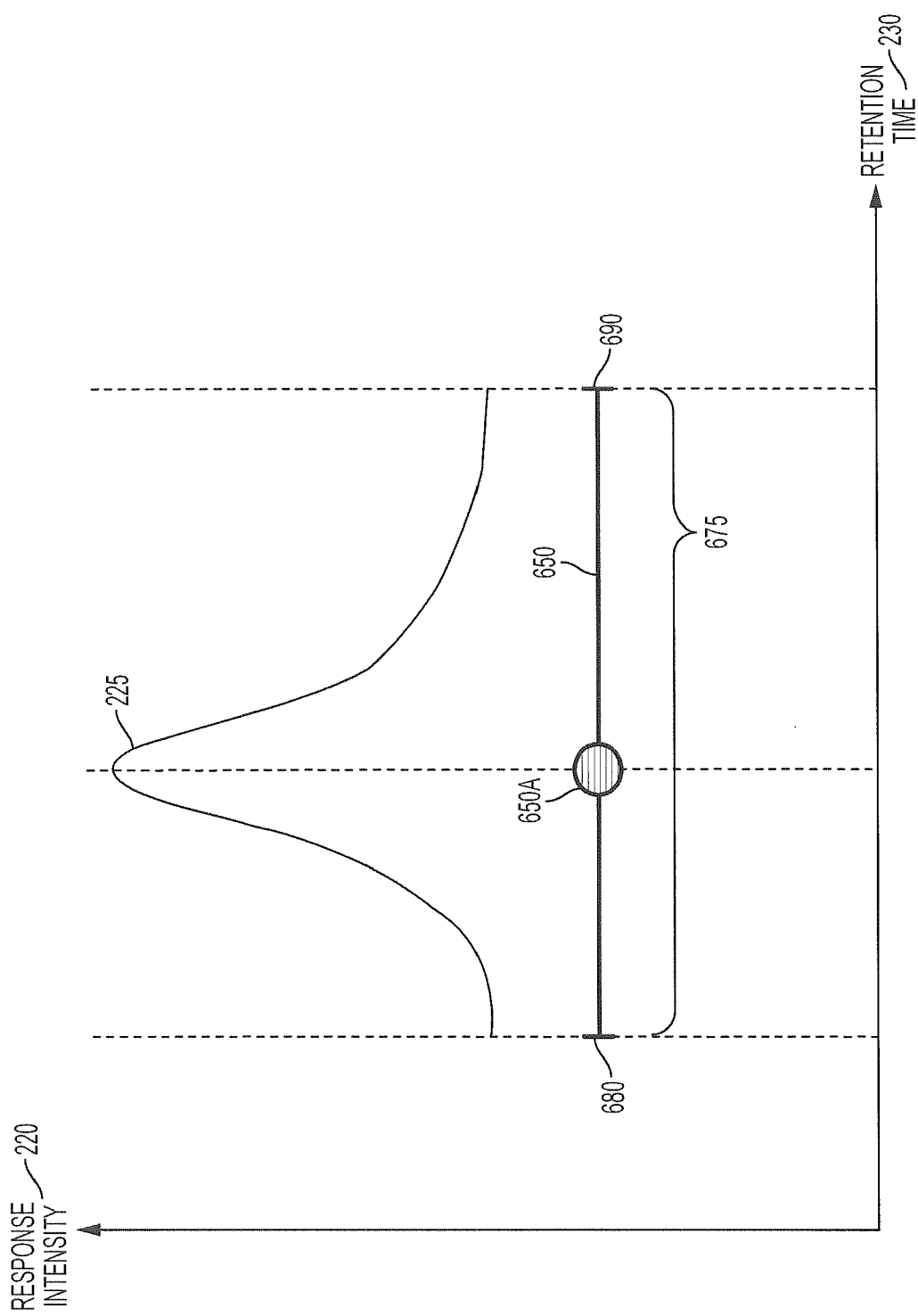
Figure 7:
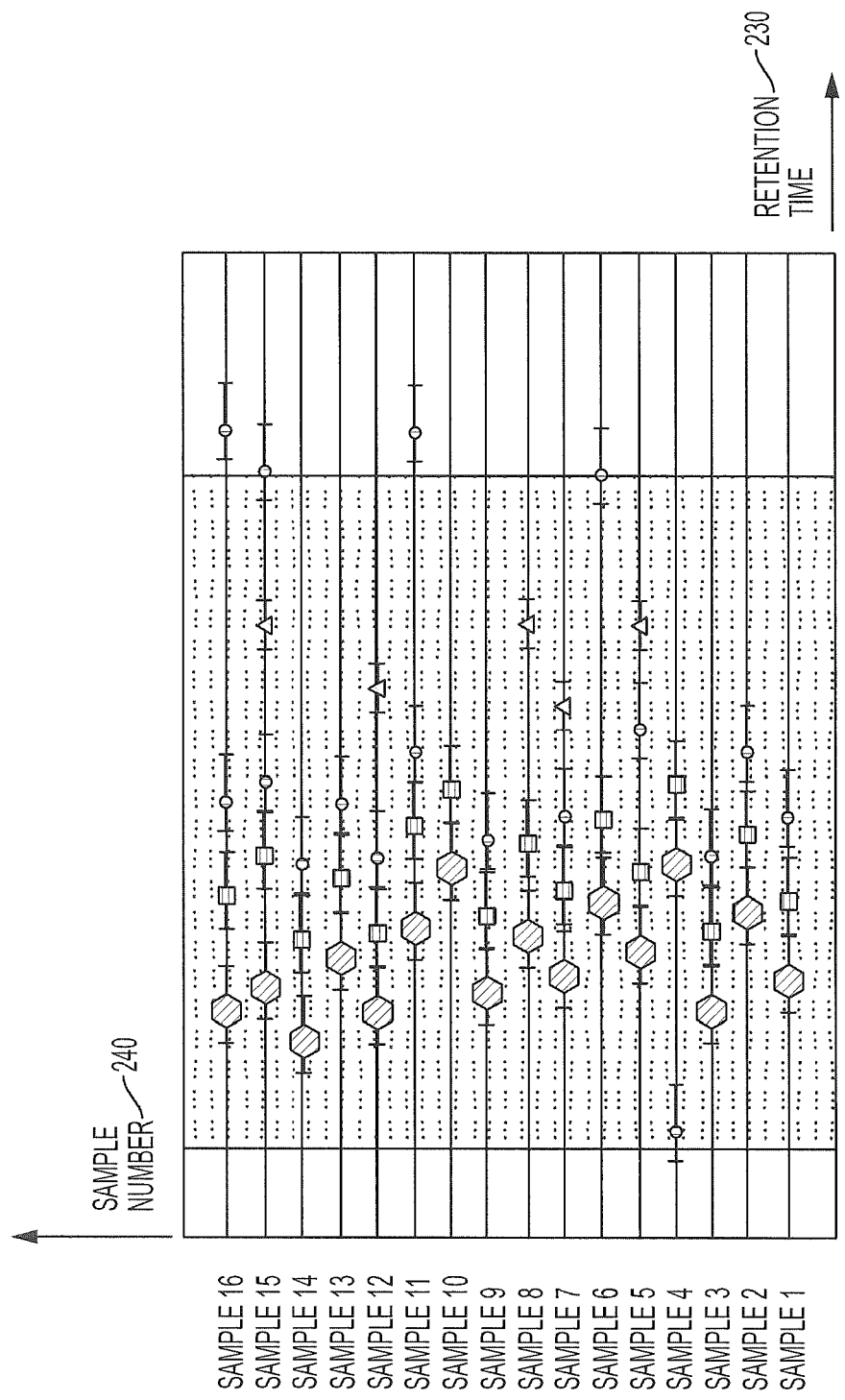
Figure 8:
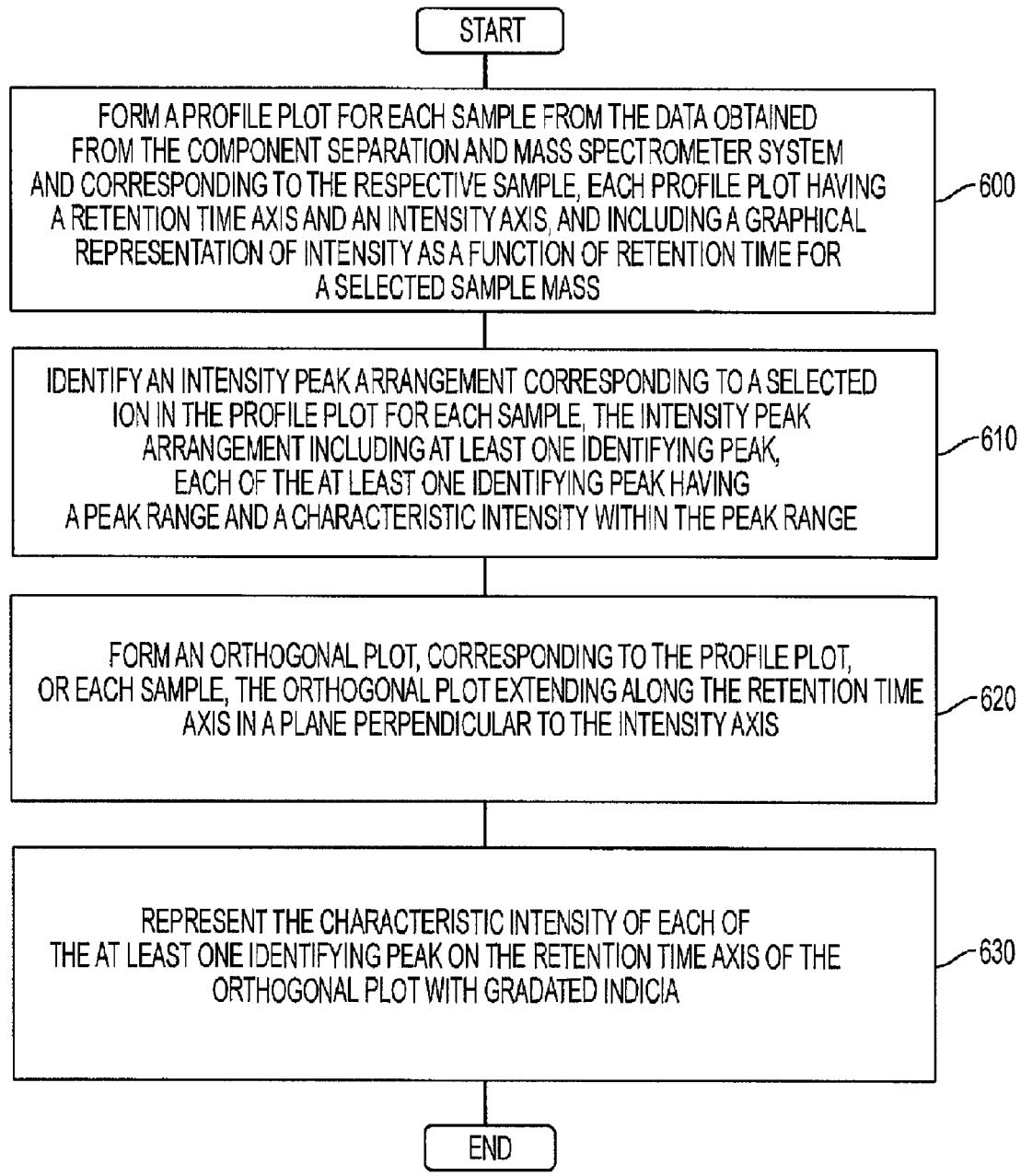
Figure 9:
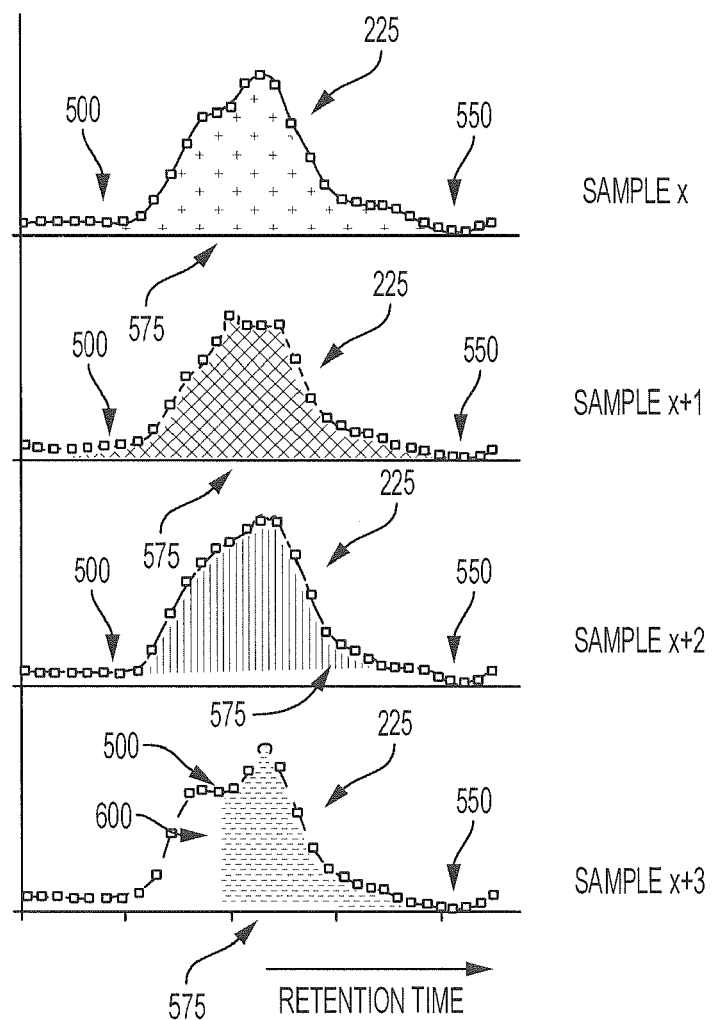
Figure 10:
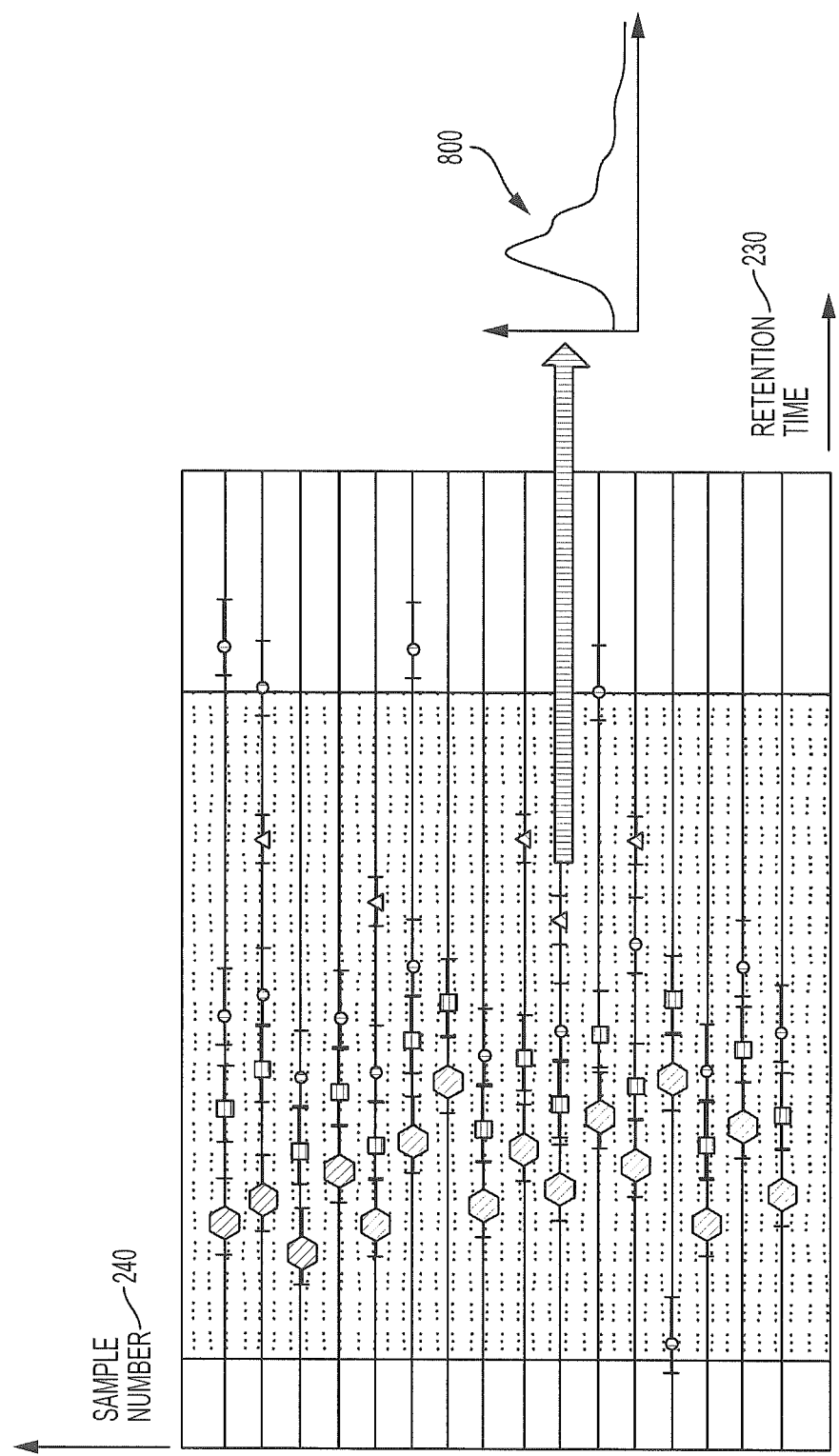
Figure 11:
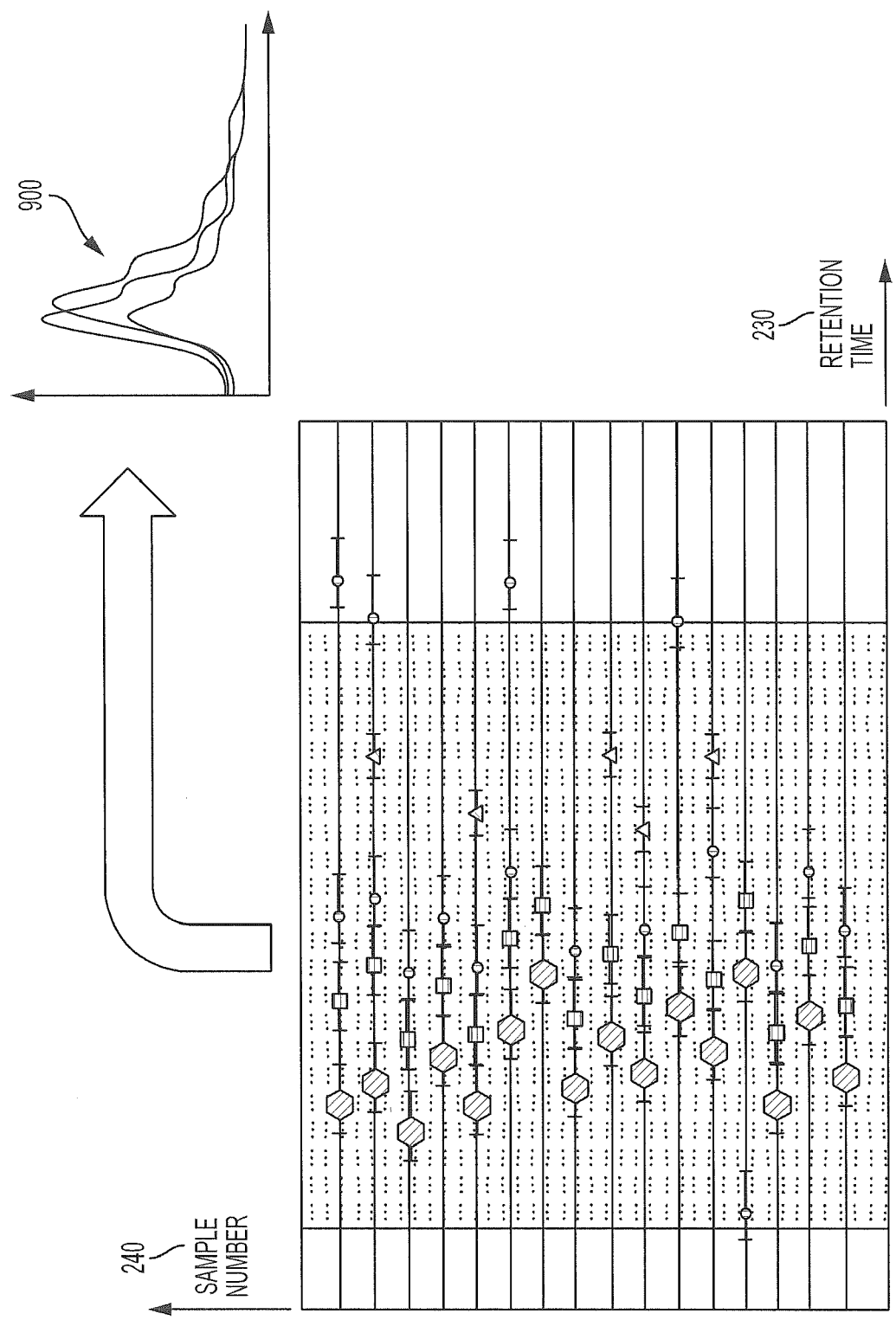

Having thus described the disclosure in general terms, reference will now be made to the accompanying drawings, which are not necessarily drawn to scale, and wherein:

FIG. 1 schematically illustrates a system according to one aspect of the present disclosure including a memory device having a database, a processor device, and a user interface (display), in communication with a spectrometry device;

FIG. 2 schematically illustrates a three-dimensional plot of spectrometry data associated with one exemplary sample;

FIG. 3 schematically illustrates a two-dimensional profile plot for one exemplary sample that may be determined from the corresponding three-dimensional plot of spectrometry data for that sample according to some aspects of the present disclosure;

FIG. 4 schematically illustrates a two-dimensional orthogonal plot corresponding to the two-dimensional profile plot for an exemplary sample shown in FIG. 3, according to some aspects of the present disclosure;

FIG. 5 schematically illustrates a two-dimensional profile plot for another exemplary sample that may be determined from the corresponding three-dimensional plot of spectrometry data for that sample according to some aspects of the present disclosure;

FIG. 6 schematically illustrates a two-dimensional orthogonal plot corresponding to the two-dimensional profile plot for an exemplary sample shown in FIG. 5, according to some aspects of the present disclosure;

FIG. 7 schematically illustrates a first across-sample plot that may be generated by some aspects of the present disclosure showing a comparison of orthogonal plots across a plurality of samples;

FIG. 8 schematically illustrates an operational flow of the apparatuses, methods, and computer program products of one exemplary aspect of the present disclosure;

FIG. 9 schematically illustrates another plot that may be generated by some aspects of the present disclosure showing a comparison of the profile plots of selected intensity peaks across a plurality of samples, wherein the determination of the area under an intensity peak or component of an intensity peak arrangement is determined according to one aspect of the present disclosure;

FIG. 10 schematically illustrates a first across-sample plot that may be generated by some aspects of the present disclosure showing a comparison of orthogonal plots across a plurality of samples, and a concurrent display of the profile plot corresponding to one of the orthogonal plots; and FIG. 11 schematically illustrates a first across-sample plot that may be generated by some aspects of the present disclosure showing a comparison of orthogonal plots across a plurality of samples, and a concurrent display of a second across-sample plot corresponding to superimposed profile plots for a selected number of samples.

DETAILED DESCRIPTION OF THE DISCLOSURE

The present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The various aspects of the present disclosure mentioned above, as well as many other aspects of the disclosure, are described in further detail herein. The apparatuses and methods associated with aspects of the present disclosure are exemplarily disclosed, in some instances, in conjunction with an appropriate analytical device which may, in some instances, comprise a separator portion (i.e., a chromatograph) and/or a detector portion (i.e., a spectrometer). One skilled in the art will appreciate, however, that such disclosure is for exemplary purposes only to illustrate the implementation of various aspects of the present disclosure. Particularly, the apparatuses and methods associated with aspects of the present disclosure can be adapted to any number of processes that are used to generate complex sets of data for each sample, across a plurality of samples, whether biological, chemical, or biochemical, in nature. For example, aspects of the present disclosure may be used with and applied to a variety of different analytical devices and processes including, but not limited to: analytical devices including a separator portion (or "component separator" portion) comprising one of a liquid chromatograph (LC) and a gas chromatograph (GC); a cooperating detector portion (or "mass spectrometer" portion) comprising one of a nuclear magnetic resonance imaging (NMR) device; a mass spectrometer (MS); and an electrochemical array (EC); and/or combinations thereof. In this regard, one skilled in the art will appreciate that the aspects of the present disclosure as disclosed herein are not limited to metabolomics analysis. For example, the aspects of the present disclosure as disclosed herein can be implemented in other applications where there is a need to characterize or analyze small molecules present within a sample or complex mixture, regardless of the origin of the sample or complex mixture. For instance, the aspects of the present disclosure as disclosed herein can also be implemented in a bioprocess optimization procedure where the goal is to grow cells to produce drugs or additives, or in a drug metabolite profiling procedure where the goal is to identify all metabolites that are the result of biotranformations of an administered xenobiotic. As will be appreciated by one skilled in the art, these exemplary applications may be very different from a metabolomics analysis, where the goal is only to examine endogenous metabolites. Some other non-limiting examples of other applications could include a quality assurance procedure for consumer product manufacturing where the goal may be to objectively ensure that desired product characteristics are met, in procedures where a large number of sample components can give rise to a particular attribute, such as taste or flavor (e.g., cheese, wine or beer), or scent/smell (e.g., fragrances). One common theme thus exhibited by the aspects of the present disclosure as disclosed herein is that the small molecules in the sample can be analyzed using the various apparatus and method aspects disclosed herein.

FIG. 1 illustrates an example of a system according to one aspect of the present disclosure wherein the system is in communication with an analytical device 110, such as a combination chromatograph (component separator)/mass spectrometer. One skilled in the art will appreciate, however, that the configurations of an analytical device 110 presented herein are for exemplary purposes only, and are not intended to be limiting with respect to the scope of suitable and appropriate analytical devices that may also be applied under the principles disclosed herein As shown, a sample (whether biological, chemical, or biochemical, in nature) 100 may be introduced into the separator portion of the analytical device 110 and analyzed using appropriate techniques, as applied through the detector portion, that will be appreciated by those skilled in the art. For example, the components of a particular sample 100 may pass through a column associated with the separator portion, at different rates and exhibit different spectral responses, as detected by the detector portion, based upon their specific characteristics. As will be appreciated by one skilled in the art, the analytical device 110 may generate a set of spectrometry data, corresponding to each sample 100 and having three or more dimensions (i.e., quantifiable samples properties) associated therewith, wherein the data included in the data set generally indicates the composition of the sample 100. In some aspects, the data set may comprise, for example, data for each sample related to retention time, sample or component (ion) mass, intensity, or even sample indicia or identity. However, such data must first be appropriately analyzed in order to determine the sample composition.

In some instances, a three-dimensional data set for each of the plurality of samples may be selected or otherwise designated for further analysis, with each dimension corresponding to a quantifiable sample property. An example of such a three-dimensional set of spectrometry data is shown generally in FIG. 2, and may be plotted on a three-axis plot or graph, with the plot or graph including individual axes for a response intensity element 220, a sample component mass element 210, and a time element 230 (particularly, in this example, the retention time or the time that a particular component spends in the column of the separator portion of the analytical device 110). The location of data points in relation to the sample component mass axis 210 may be indicative, for example, of the number of individual component molecules within the sample 100 and the relative mass values for such sample components. According to other aspects of the present disclosure, other analytical devices may be used to generate a three or more dimensional set of analytical data corresponding to the sample 100. For example, the analytical device may include, but is not limited to: various combinations of a separator portion comprising one of a liquid chromatograph (LC) (positive or negative channel) and a gas chromatograph (GC); and a cooperating detector portion comprising one of a nuclear magnetic resonance imaging (NMR) device; a mass spectrometer (MS); and an electrochemical array (EC). One skilled in the art will appreciate that such complex three or more dimensional data sets may be generated by other appropriate analytical devices that may be in communication with components of aspects of the present disclosure as described in further detail herein.

A plurality of samples 100 may be taken individually from a well plate 120 and/or from other types of sample containers and introduced individually into the analytical device 110 for analysis and generation of the corresponding three or more dimensional data set (see, e.g., FIG. 2). For example, individual samples 100 may be transferred from a well plate 120 to the analytical device 110 via pipette, syringe, microfluidic passageways defined by a test array, and/or other systems for transferring samples in a laboratory environment. As disclosed herein, the nature of the samples may, vary considerably, generally comprising mixtures or complex mixtures including small molecules, wherein such samples may exemplarily include, but are not limited to: blood samples, urine samples, cell cultures, saliva samples, plant tissue and organs (e.g., leaves, roots, stems, flowers, etc.), plant extracts, culture media, membranes, cellular compartments/organelles, cerebral spinal fluid (CSF), milk, soda products, food products (e.g., yogurt, chocolate, juice), and/or other types of biological, chemical, and/or biochemical samples in which the metabolites and/or chemical/molecular components of interest may be present.

As shown in FIG. 1, aspects of the present disclosure may comprise a database (e.g., a relational database) stored at least in part, for example, as executable instructions in a memory or memory device 140 (i.e., a computer-readable storage medium having computer-readable program code portions stored therein), wherein the memory device 140 is in communication with a processor or processor device 130 (e.g., a computer device implementing a processor) for selectively executing the instructions/computer-readable program code portions in the memory device 140 to cause an apparatus to perform particular method steps and/or functions. In some instances, the memory device 140 and/or the processor device 130 may be configured to be in communication with the analytical device 110 for automatically receiving a data set (in some instances, a data set comprising three or more dimensions, wherein a data parameter such as sample indicia, sample or component (ion) mass, retention time, and intensity/response may represent one of the dimensions of the data set), corresponding to each of the plurality of samples 100, therefrom. The processor device 130 may be in communication with the analytical device 110 via wire line (RS-232, and/or other types of wire connection) and/or wireless (such as, for example, RF, IR, or other wireless communication) techniques such that the database associated with the memory device 140/processor device 130 (and/or in communication therewith) may receive the data set from the analytical device 110 so as to be stored thereby Furthermore, the analytical device 110 may be in communication with one or more processor devices 130 (and associated user interfaces or displays 150) via a wire line and/or wireless computer network including, but not limited to: the Internet, local area networks (LAN), wide area networks (WAN), or other networking types and/or techniques that will be appreciated by one skilled in the art. The user interface/display 150 may be used to display any or all of the communications involving the system, including the manipulations and analyses of sample data disclosed herein, as will be understood and appreciated by one skilled in the art. The database may be structured using commercially-available software, such as, for example, Oracle, Sybase, DB2, or other database software. As shown in FIG. 1, the processor device 130 may be in communication with the memory device 140 (such as a hard drive, memory chip, flash memory, RAM module, ROM module, and/or other memory device 140) for storing/administering the database, including the three-dimensional data sets automatically received from the analytical device 110. In addition, the memory device 140 may also be used to store other received data in the database and/or data otherwise manipulated by the processor device 130.

The processor device 130 may, in some aspects, be capable of converting each of the data sets (see, e.g., FIG. 2, wherein the exemplary data set is a three-dimensional data set) for each of the samples, received by the memory device 140, into at least one corresponding two-dimensional data set (see, e.g., FIG. 3), wherein the at least one two-dimensional data set may comprise, for example, a two-dimensional component "profile" of a particular sample 100 at a particular point 235 (FIG. 2) along one of the three axes of the three-dimensional data set. The particular point 235 along one of the three axes may be, for example, a particular sample component mass along the sample component mass axis 210. The resulting profile (also referred to herein as a "profile plot" as shown in FIGS. 3 and 5) illustrates that particular sample component mass detected (and the intensity of that detection) as a function of time measured from a zero point, the zero point corresponding to when the sample 100 is injected and/or otherwise introduced into the analytical device 110). For example, the processor device 130 may be configured to produce a sample component (retention) time versus intensity/response profile of the sample for that given or selected sample component mass point 235 (see FIGS. 3 and 5, for example). The "x" axis in FIG. 2 (or time axis 230, for example) may further, in some instances, be characterized as a retention index and/or a retention time. Thus, the processor device 130 may be further capable of parsing each of the three (or more) dimensional data sets, for each of the plurality of samples, into one or more individual two-dimensional (i.e., sample component retention time versus intensity/response profile) profiles corresponding to at least one particular (selected) sample component mass point (element 235, for example) so as to convert each three (or more) dimensional data set (of FIG. 2, for example) into at least one corresponding two-dimensional data set of a selected sample component (having a profile or profile plot shown, for example, in FIGS. 3 and 5, and step 600 in FIG. 8) that may further be plotted as an response intensity 220 of the corresponding sample component mass versus a sample component retention time 230, and displayed on the user interface/display 150, as desired.

According to some aspects, the processor device 130 may be configured to selectively execute the executable instructions/computer-readable program code portions stored by the memory device 140 so as to accomplish, for instance, the identification, quantification, representation, and/or other analysis of a selected sample component (i.e., a metabolite, molecule, or ion, or portion thereof) in each of the plurality of samples, from the two-dimensional data set representing that selected sample component. In doing so, the sample component to be analyzed is first determined by selecting an intensity peak (see, e.g., element 225 in FIG. 5) or intensity peak arrangement (see, e.g., element 225 in FIG. 3) generally present with sufficient quality in each of the plurality of two-dimensional data sets (i.e., across the plurality of samples) of metabolomics data (i.e., "at least one identifying peak"). As previously disclosed, such two-dimensional data sets are determined from respective three or more dimensional data sets of metabolomics data for each of a plurality of samples, generally by selecting or otherwise designating two desired dimensions/axes, and selecting a particular value (i.e., retention time or sample component mass) with respect to another one of the dimensions/axes of the three or more dimensional data set. One skilled in the art will appreciate, however, that the sample component to be analyzed may, in some instances, be selected from the three or more dimensional data set, if necessary or desired, and that such selection of the sample component to be analyzed may be further refined upon analysis of the two-dimensional data set corresponding thereto. In some instances, the selection of the sample component to be analyzed may be facilitated, for example, by analyzing a graphical representation of the three or more dimensional data set(s) (i.e., via user interface or display 150, which may comprise, for example, a display device, personal computer, and/or other electronic device having a display for graphical representation of data), and the selection may involve, for instance, evaluating the apparent response intensity of that sample component in the respective two-dimensional and/or three or more dimensional data sets, to determine the selected intensity peak or intensity peak arrangement 225 (i.e., "at least one identifying peak").

In some instances, the processor device 130 may be configured to execute computer-readable program code portions stored by the memory device 140 for analyzing the collected data sets across two or more of the plurality of samples so as to determine a suitable sample component to be further analyzed, whether that sample component has been previously identified (i.e., as a particular molecule, ion, or metabolite, or portion thereof) or not, via an intensity peak or combination or arrangement of intensity peaks (also referred to herein as an "intensity peak arrangement") 225. The intensity peak(s) or combinations thereof otherwise may be referred to herein as "at least one identifying peak," "selected intensity peak," "selected intensity peak arrangement," "ion peak,", or "selected ion peak" associated therewith. That is, in order to select a suitable sample component for analysis, the processor device 130 may be configured to sort and/or group intensity/ion peak data across the plurality of samples, for example, by sample component mass and/or by selected retention time. In this manner, the processor device 130 may also be configured, for instance, to examine intensity peak or intensity peak arrangement data that is sufficiently discernible from background noise or other undesirable data artifacts (i.e., of suitable quality), in order to reduce variances and provide a more statistically significant analysis upon determining the selected intensity peak or intensity peak arrangement 225 (i.e., "at least one identifying peak"). As referred to herein, an "intensity peak arrangement" or combination of intensity peaks 225 may comprise, for example, a "main peak" 225A and at least one "sub-peak" 225B, 225C, 225D following on the retention time axis (see, e.g., FIG. 3). Such an "intensity peak arrangement" or combination of intensity peaks 225 may result, for example, from instances of co-elution in high throughput processing of samples through the analytical device(s). With such high throughput processing, the intensity peaks representing the various metabolites may not be detected by the analytical device(s) in such a manner as to appear "well separated" (i.e., "well resolved") from each other in the resulting data, and may thus appear as groups of intensity peaks as shown, for example, in FIG. 3. In some cases, the at least one sub-peak 225B, 225C, 225D may have a lesser intensity/response than the main peak 225A, though not necessarily always evident. In other cases, one or more of the at least one sub-peak may be evident prior to the main peak 225A on the retention time axis 230. In instances where a metabolite is distinct from others in the sample (i.e., "well separated" or "well-resolved"), or in instances where the analytical device(s) receive the samples under favorable conditions, the intensity peaks representing the various metabolites may be detected by the analytical device(s) in such a manner as to appear "w well-separated/well-resolved" from each other in the resulting data, and may thus appear as a separate, distinct, and/or discrete intensity peak as shown, for example, in FIG. 5.

In one aspect, in order to determine the selected intensity peak or intensity peak arrangement, the processor device 130 may be configured to first identify a plurality of candidate intensity peaks or intensity peak arrangements in each of the two-dimensional data sets, and compare the candidate intensity peaks or intensity peak arrangements across the plurality of two-dimensional data sets, wherein the candidate intensity peak or intensity peak arrangement with the lowest standard deviation (i.e., the best data quality of the main peak 225A across the plurality of samples) may be selected as the selected intensity/ion peak or intensity/ion arrangement 225 (see, e.g., step 610 in FIG. 8). However, one skilled in the art will appreciate that the selected intensity peak or intensity peak arrangement may be determined in other manners. For example, upon comparing the candidate intensity peak arrangements across the plurality of two-dimensional data sets (i.e., across the plurality of samples), one of the candidate intensity peaks or intensity peak arrangements evident across the plurality of two-dimensional data sets, and corresponding to a recognized compound, metabolite, ion, or component or portion thereof in an associated database of such compounds, metabolites, ions, or components or portions thereof, may be selected as the selected intensity/ion peak or intensity peak arrangement. More particularly, for instance, the candidate intensity peaks or intensity peak arrangements across the plurality of two-dimensional data sets may be compared with mass spectra included in a library or database of recognized or otherwise known compounds (i.e., using a library or database matching process), followed with subjective curation or resolution of the matching process, if necessary. In such an instance, one of the candidate intensity peaks or intensity peak arrangements matched with, corresponding to, or best correlated with, the recognized or known compound (i.e., by comparison of quantitative mass) may be selected as the selected intensity/ion peak or intensity peak arrangement 225 as shown, for example, in FIGS. 3 and 5, and may facilitate or otherwise promote consistent analysis across the plurality of samples.

In particular aspects, the processor device 130 may further be configured to execute instructions/computer readable program code portions so as to identify a particular compound or sample component (i.e., a metabolite) associated with the selected and analyzed intensity peak or intensity peak arrangement 225). The particular compound/sample component may be "known named" and/or "known, but unnamed" chemicals/compounds. That is, for example, the identified particular compound/sample component may correspond to a metabolite having a chemical nomenclature or to a "known, but unnamed" metabolite which has been previously identified, but not yet assigned a chemical name and/or classification. One skilled in the art will appreciate that such compound identification procedures may be accomplished in many different manners with respect to the selected intensity peak/intensity peak arrangement 225 and/or the corresponding two-dimensional or three-dimensional data set, in some instances, across the plurality of samples under analysis. For example, some compound identification procedures are disclosed in U.S. Pat. No. 7,433,787 (System, Method, and Computer Program Product Using a Database in a Computing System to Compile and Compare Metabolomic Data Obtained From a Plurality of Samples); U.S. Pat. No. 7,561,975 (System, Method, and Computer Program Product for Analyzing Spectrometry Data to Identify and Quantify Individual Components in a Sample); and U.S. Pat. No. 7,949,475 (System and Method for Analyzing Metabolomic Data), all assigned to Metabolon, Inc., which is also the assignee of the present application. To the extent that such compound identification procedures are relevant to the disclosure herein, such compound identification procedures disclosed by U.S. Pat. Nos. 7,433,787; 7,561,975; and 7,949,475 are incorporated herein by reference, and not otherwise discussed in detail herein for the sake of brevity.

The processor device 130 may be further configured to align the selected intensity peak or intensity peak arrangement 225 evident in each two-dimensional data set, across the plurality of samples, prior to further analysis of the data. More particularly, when analyzing spectrometry data across a plurality of samples, various compounds (including metabolites) may move at somewhat different rates during a separation process, from one sample to another, so that it may not be entirely clear which peaks or peak arrangements (corresponding to eluted or co-eluted compounds, for example) should be considered as corresponding to one another across the plurality of samples. As such, the processor device 130 may be configured to execute instructions/computer readable program code portions to implement an intensity peak/peak arrangement alignment correction method for the selected intensity peak or peak arrangement in each two-dimensional data set across the plurality of samples. For example, one such method involves spiking known compounds into each sample that are characterized by known retention times (RT) in spectrometry analysis. The set of "spiked" compounds matches a fixed retention index (RI) value to the shifting RT. The "spiked" compounds thus provide an internal standard (IS) that may be used to align data from a plurality of samples from study to study and/or from study to a chemical library. One skilled in the art will appreciate, however, that many different methods may be used to perform the intensity peak/peak arrangement alignment for the selected intensity peak or peak arrangement, across the plurality of samples, within the spirit and scope of the present disclosure, and that the example presented herein in this respect is not intended to be limiting in any manner.

Once the sample component to be analyzed has been selected, and aligned via the corresponding selected intensity peak/peak arrangement across the plurality of samples, the processor device 130 may be configured to execute instructions/computer readable program code portions to implement a procedure for determining an area associated with the selected intensity peak or the selected peak arrangement or component thereof, using one of a plurality of integration procedures, for each of the two-dimensional data sets across the plurality of samples (see, e.g., the area represented by the shaded portions of each of the 4 profile plots for 4 different samples shown in FIG. 9). In such instances, the area of the selected intensity peak or the selected peak arrangement (or component thereof) 225 may represent, for example, a relative quantity of the corresponding sample component (i.e., molecule, ion, or metabolite or portion thereof) within the sample, for example, in terms of a percent relative standard deviation (% RSD), since each two-dimensional data set is configured to indicate a sample property (i.e., sample component (retention) time) in one dimension versus a detected intensity at a selected value of another sample property (i.e., sample component mass) as a function of time in the other dimension. In such instances, the intensity may represent, for example, an amount of the molecules, ions, or metabolites or portion or component thereof having the selected value of the sample component mass, detected as a function of (retention) time, beginning from a time zero point.

In determining the area associated with the selected intensity peak or the selected peak arrangement or component thereof 225 in each two-dimensional data set, the boundaries of that intensity peak (or component of an intensity peak arrangement) along the respective axes of the profile plot must first be determined. In doing so, the processor device 130 may be configured to execute instructions/computer readable program code portions to determine an intensity peak origin 500 and an intensity peak terminus 550 of the intensity peak (whether discrete/standing alone, or as a component of an intensity peak arrangement) along the time dimension (i.e., the sample component time axis 230) of the two-dimensional data set (see, e.g., FIG. 9). In this regard, each of the intensity peak origin 500 and the intensity peak terminus 550 may not necessarily be clearly defined. That is, other sample components, background noise, or other undesirable data artifacts may sometimes impinge on or interfere with the selected intensity peak 225 in a data set, in the form of a "shoulder" or other transition about either the apparent intensity peak origin 500 or intensity peak terminus 550. As such, the determination of the intensity peak origin 500 and/or the intensity peak terminus 550 may also involve some approximations or subjective analysis such as, for example, determining a particular change in slope or other threshold change, wherein some variations may be permissible within certain tolerances without significantly affecting data quality (i.e., from a statistical perspective). Along with determining the intensity peak origin 500 and/or the intensity peak terminus 550, relative data may also be determined such as, for example, the relationship of the selected (actual) intensity peak 225 in relation to the intensity peak origin 500 and/or the intensity peak terminus 550. Such a relationship between the selected (actual) intensity peak 225 and the intensity peak origin 500 and/or the intensity peak terminus 550 may indicate, for instance, a shape of the area under the curve of intensity magnitude as a function of time (i.e., extending along the time dimension 220), as well as, for example, the magnitude of the area under the curve of intensity magnitude as a function of time, itself.

According to one aspect of the present disclosure, once the intensity peak origin 500 and the intensity peak terminus 550 have been determined for the selected intensity peak (or the selected intensity peak arrangement or component thereof) 225 in each two-dimensional data set, the relation of each of the intensity peak origin 500 and the intensity peak terminus 550, with respect to a baseline intensity 575 in the intensity dimension 220, must also be determined in order to determine the area of the selected intensity peak, or the selected intensity peak arrangement or component thereof. Details and disclosure regarding the determination of the baseline intensity (noise), as well as the integration procedure used to determine the area under the curve, are disclosed, for example, in U.S. Patent Application Publication No. US 2012/0239306 to Dai et al. and assigned to Metabolon, Inc., also the assignee of the present disclosure, the contents of which are incorporated herein in their entirety by reference. As such, one aspect of an analysis herein generally involves determining an identity peak or characteristic intensity for the selected ion from at least one identifying peak (i.e., the main peak and the at least one sub-peak), and determining an area associated with the identity peak/characteristic intensity for the selected ion, using an integration (mathematical calculation of area) procedure, wherein the determined area of the identity peak/characteristic intensity is associated with a relative quantity of the selected ion corresponding thereto in the respective sample.

Another aspect of the present disclosure comprises a method of analyzing data for a plurality of samples obtained from a component separation and mass spectrometer system (see, e.g., FIG. 9), wherein the data includes a data set for each sample, and wherein each data set includes, for example, a sample indicia, a sample ion mass, a retention time, and an intensity, as otherwise disclosed herein. In such an aspect, a profile plot (see, e.g., FIGS. 3 and 5) may be formed for each sample from the data obtained from the component separation and mass spectrometer system, and corresponding to the respective sample, as previously disclosed. Each such profile plot for each sample may include a retention time axis 230 and an intensity axis 220, and may provide a graphical representation of intensity as a function of retention time for a selected sample ion mass or sample component mass (step 600, FIG. 8). The method may also include identifying an intensity peak or intensity peak arrangement 225 (i.e., "at least one identifying peak") corresponding to a selected ion or components of a selected ion in the profile plot for each sample (step 610, FIG. 8). In some aspects, as shown, for example, in FIG. 3, the at least one identifying peak or intensity peak arrangement may include a main peak 225A and at least one sub-peak (see, e.g., 225B, 225C, 225D, etc.). In some instances, the at least one sub-peak may occur successively to the main peak 225A. However, in other instances, one or more of the at least one sub-peak may occur or otherwise be evident prior to the occurrence of the main peak 225A. In other aspects, as shown, for example, in FIG. 5, the at least one identifying peak may comprise a single "well separated" or "well-resolved" intensity peak 225 that may be apparent as a separate, distinct, and/or discrete intensity peak. The well-separated/well-resolved intensity peak 225 (FIG. 5) or the main peak 225A and each of the at least one sub-peak (225B, 225C, 225D, etc.) (FIG. 3) may each be characterized as having a peak range and a characteristic intensity within that peak range. The characteristic intensity of the well-separated/well-resolved intensity peak 225, or the main peak 225A and each of the at least one sub-peak (225B, 225C, 225D, etc.), may be designated according to a particular intensity observed at a characteristic retention time (or within a retention time range) and, in some instances, according to an expected intensity (or intensity range) at the characteristic retention time.

Once the (two-dimensional) profile plot for each sample has been determined, particular aspects of the present disclosure also involve forming an orthogonal plot 650 (see, e.g., FIGS. 4 and 6), corresponding to the profile plot, for each sample (FIGS. 4 and 6, and step 620, FIG. 8). Such an orthogonal plot 650 generally extends along the retention time axis 230 in a plane perpendicular to the intensity axis 220. That is, the orthogonal plot 650 may be characterized as a view of the profile plot along the x-axis (retention time axis 230) from a perspective parallel to the y-axis (intensity axis 220), wherein the viewed plane extends along the x-axis, perpendicularly to the y-axis. See, e.g., FIGS. 4 and 6. For example, such an orthogonal view may be characterized as a view from along the x-axis in the increasing direction of the y-axis, from y=0, or a view of the x-axis in the decreasing direction of the y-axis, from y>0. In a basic form, the orthogonal view may also appear as a "two-dimensional" view, with the y-axis being represented by a point, and the view of the sample data for the particular component mass appearing as a line co-extensive with the x-axis. However, an additional aspect of the present disclosure may comprise representing the characteristic intensity of each of the well-separated intensity peak 225, or the main peak 225A and the at least one sub-peak (225B, 225C, 225D, etc.), on the retention time axis 220 of the orthogonal plot with discernible indicia (see, e.g., elements 650A, 650B, 650C, and 650D in FIG. 4, and element 650A in FIG. 6, and step 630, FIG. 8). In some instances, such discernible indicia may comprise, for example, gradated indicia having, for instance, a maximum expression for the characteristic intensity of the main peak 650A and a lesser expression for the characteristic intensity of each of the at least one sub-peak (650B, 650C, 650D, etc.). Such gradated indicia may also be applicable in instances of a well-separated/well-resolved intensity peak 225, as shown, for example, in FIG. 6, wherein the discernible indicia may represent the characteristic intensity of the well-separated/well-resolved intensity peak 225 in relation to a legend or other catalog of such gradated indicia. Such gradated indicia may include, for example, a particular shape or object that is gradated in size for the characteristic intensities based upon, for instance, the intensity magnitude of each of the characteristic intensities. That is, the characteristic intensity of each of the main peak and the at least one sub-peak on the retention time axis of the orthogonal plot, may be represented with a gradated shape having a maximum size of the shape for the characteristic intensity of the main peak and a lesser size of the shape for the characteristic intensity of each of the at least one sub-peak. For the well-separated/well-resolved intensity peak, the indicia may be gradated, for example, according to the magnitude of the characteristic intensity thereof in a given range (i.e., the closer the characteristic intensity is to the maximum of the range, the greater the gradation of the indicia for the well-separated/well-resolved peak on the orthogonal plot)

In one such aspect, the shape may be a circle or oval (see, e.g., FIGS. 4 and 6), wherein, as shown in FIG. 4, the characteristic intensity of the main peak 650A may be represented by the largest size circle (i.e., the maximum expression of this shape) placed at the retention time along the retention time axis corresponding to the characteristic intensity (i.e., the highest intensity magnitude) of the main peak 650A. The at least one sub-peak (650B, 650C, 650D, etc.) may further be represented by gradually lesser-sized circles (i.e., lesser expressions of this shape) for each sub-peak, with each such lesser-sized circle being placed at the retention time along the retention time axis corresponding to the characteristic intensity (i.e., a lesser intensity magnitude) of the respective at least one sub-peak. One skilled in the art will appreciate, however, that the main peak and the at least one sub-peak of the selected intensity peak arrangement 225 may not necessarily correspond in gradation to the intensity magnitude. That is, there may be some instances where the main peak identifying the ion or intensity peak arrangement may not necessarily have the highest intensity in the intensity peak arrangement. Accordingly, in such instances, the succession or gradation between the main peak and the at least one sub-peak may be based, for example, on the relative importance of the respective characteristic intensity peaks in identifying the ion/intensity peak arrangement 225. In some instances, as shown in FIG. 6, a well-separated intensity peak 225 may be an indicia, such as a circle or oval, that is gradated according to the particular characteristics of that intensity peak according to a predefined or preselected range or criteria (i.e., the illustrated circle 650A representing the well-separated intensity peak 225 may be the largest circle available in the defined gradation of the indicia, which signifies that the characteristic intensity is at or about the highest intensity expected for that intensity peak).

In other aspects or the present disclosure, the disclosed indicia may include other indicia instead of or in addition to the shape indicia. For example, as shown in FIG. 7, indicia comprising different shapes may be used to indicate the main peak and the at least one sub-peak (i.e., a circle for the main peak, followed by a triangle for the next sub-peak, followed by a square for the still-next sub-peak, etc.), or the characteristic(s) of the well-separated intensity peak in relation to the defined gradation. That is, the characteristic intensity of each of the main peak and one of the at least one sub-peak on the retention time axis of the orthogonal plot may be represented with different shapes, including a first shape for the characteristic intensity of the main peak and a second shape for the characteristic intensity of the one of the at least one sub-peak, or the well-separated intensity peak may be represented by a particular shape in relation to the magnitude of the characteristic intensity of that peak. In another example, the indicia may comprise a shape outline, wherein the outline is filled with a gradated color, shade, hue, or other progression for the main peak and the at least one sub-peak, or according to the characteristic(s) of the well-separated intensity peak in relation to the defined gradation. More particularly, for instance, the largest circular outline representing the main peak may be filled with the darkest (i.e., the highest intensity magnitude) of a selected color, with the color becoming lighter (i.e., a lesser intensity magnitude) for the successive sub-peaks. Instead of a color, a grayscale may be used, for instance, with black representing the main peak (i.e., the highest intensity magnitude) and shades of gray (i.e., a lesser intensity magnitude) used to represent the successive sub-peaks. Otherwise, the well-separated intensity peak may be represented by a particular color, shade, hue, or other indicia within the progression in relation to the magnitude of the characteristic intensity of that peak. That is, the characteristic intensity of each of the main peak and the at least one sub-peak on the retention time axis of the orthogonal plot may be represented with a gradated shading, color, hue, etc. having a maximum intensity of the shading, color, hue, etc. for the characteristic intensity of the main peak and a lesser intensity of the shading, color, hue, etc. for the characteristic intensity of each of the at least one sub-peak, or according to the characteristic(s) of the well-separated intensity peak in relation to the defined gradation. Otherwise, one skilled in the art will appreciate that the process of distinguishing the characteristic intensity of the main peak from the characteristic intensity of the at least one sub-peak, and/or the characteristic intensity of the sub-peaks from each other, as well as representing the characteristic(s) of the well-separated intensity peak in relation to the defined gradation, may be accomplished in many different manners, in the alternative or in addition to the manners disclosed herein with respect to shape, outline, color, shade, hue, other progression, etc. For example, "three-dimensional" effects could also be implemented in connection with the indicia, such that each indicia representing the main peak and the at least one-sub-peak is configured to project outwardly from the orthogonal plot, for example, in proportion to the characteristic intensity of the respective one of the main peak and the at least one sub-peak, or according to the characteristic (s) of the well-separated intensity peak in relation to the defined gradation of the three-dimensional effect.

In some aspects, in addition to the representation of the characteristic intensity 650A, 650B, 650C, 650D of each of the main peak and the at least one sub-peak ("the at least one identifying peak") on the orthogonal plot, the method may also include representing the peak range 675A, 675B, 675C, 675D of each of the main peak and the at least one sub-peak on the orthogonal plot with range indicia, or the peak range 675 of the well-separated peak 225 (see, e.g., FIG. 6), with the range indicia having a first indicium 680 (see, e.g., FIGS. 4 and 6) representing an initiation of the peak range (i.e., the intensity peak origin 500) and a second indicium 690 (see, e.g., FIGS. 4 and 6) representing a termination of the peak range (i.e., the intensity peak terminus 550), for the main peak and each of the at least one sub-peak, or for the well-separated intensity peak, of the selected intensity peak arrangement 225 for each sample. In such instances, the peak range may be provided in addition to or in the alternative to the characteristic intensities of the main peak and the at least one sub-peak, or the well-separated intensity peak. Where the characteristic intensity is provided in addition to the peak range, the characteristic intensity 650A, 650B, 650C, 650D (or characteristic intensity 650A for the well-separated peak) generally falls between the corresponding intensity peak origin 500, 680 and intensity peak terminus 550, 690.

In some aspects, the relation between the characteristic intensity 650A, 650B, 650C, 650D, and the corresponding intensity peak origin 500, 680 and intensity peak terminus 550, 690 of the peak range of the corresponding one of the main peak or the at least one sub-peak (or the well-separated/well-resolved peak) may be indicative of properties or characteristics of the intensity as a function of retention time (for a particular sample component mass) on the corresponding profile plot That is, the relationship of the peak range to the characteristic intensity, and/or the relationship of the peak range of one component of the intensity peak arrangement and the peak range of an adjacent component of the intensity peak arrangement, may indicate, for example, a shape of the particular main peak or the at least one sub-peak (or the well-separated/well-resolved peak) and/or the area of the main peak or the at least one sub-peak (or the well-separated/well-resolved peak) under the plotted intensity as a function of time. More particularly, for example, a characteristic intensity disposed approximately medially between an intensity peak origin and an intensity peak terminus (and if the intensity peak origin does not also comprise the intensity peak terminus of an adjacent preceding peak or sub-peak, or the intensity peak terminus does not comprise the intensity peak origin of an adjacent subsequent peak or sub-peak) may signify that the particular peak is a "stand alone," "well-separated," or "well-resolved" intensity peak that is generally symmetrical on either side of the intensity peak (i.e., similar to a symmetrical bell curve). Under similar conditions, if the characteristic intensity is shifted toward either the intensity peak origin or the intensity peak terminus, the "stand alone," "well-separated," or "well-resolved" intensity peak may be skewed accordingly (i.e., the bell curve is skewed or shifted away from symmetry). The area under the intensity curve (indicative of the amount of the ion of other component in the intensity peak arrangement) may thus be determined by various integration (mathematical) techniques used for determining the area under such a curve or function.

If the intensity peak origin of a particular peak range does also comprise the intensity peak terminus of an adjacent preceding peak or sub-peak, or if the intensity peak terminus does comprise the intensity peak origin of an adjacent subsequent peak or sub-peak, such a relationship may indicate that the adjacent preceding peak or sub-peak, or the adjacent subsequent peak or sub-peak, may comprise, for example, a "shoulder peak," "secondary peak," or other transition about either the intensity peak origin 500 or the intensity peak terminus 550 (see, e.g., FIG. 4). That is, the peak range of each of the main peak and the at least one sub-peak may be represented on the orthogonal plot with range indicia, with the second indicium of the range indicia of the main peak also representing the first indicium of the range indicia of a next successive sub-peak of the intensity peak arrangement, which indicates that the next successive sub-peak is one of a shoulder peak and a secondary peak associated with the main peak. Moreover, the peak range of each of the main peak and the at least one sub-peak may be represented on the orthogonal plot with range indicia, with the second indicium of the range indicia of one of the sub-peaks also representing the first indicium of the range indicia of a next successive sub-peak of the intensity peak arrangement, which indicates that the next successive sub-peak is one of a shoulder peak and a secondary peak associated with the one of the sub-peaks.

The particular location of the characteristic intensity 650A, 650B, 650C, 650D along the retention time axis for either of the adjacent preceding peak or sub-peak, or the adjacent subsequent peak or sub-peak, may also serve to identify the particular nature of the sub-peak (i.e., as a shoulder peak, secondary peak, or other transition, etc.), as well as the skew thereof. The area under the intensity curve (indicative of the amount of the ion of other component in the intensity peak arrangement) may thus be determined by various integration techniques used for determining the area under such a curve or function related to, for example, a shoulder peak, secondary peak, or other transition, as disclosed, for instance, in U.S. Patent Application Publication No. US 2012/0239306 to Dai et al. otherwise incorporated herein in its entirety by reference.

Accordingly, the representation of the sample data on the orthogonal plot, for the corresponding profile plot, may be appropriately configured such that the implementation thereof indicates additional "dimensions," sample properties, or other information, over the mere two-dimensional representation afforded by the orthogonal plot. For example, in such instances, the "two-dimensional" orthogonal plot may be provided with appropriate indicia to indicate, for example, additional "dimensions" such as peak area and peak shape, which may be useful to one skilled in the art for expediting interpretation and analysis of the sample data.

In further aspects of the present disclosure, the selected intensity peak or peak arrangement 225 may be compared or otherwise analyzed across any or all of the various samples. In such instances, the processor device 130 may further be configured to execute instructions/computer readable program code portions so as to arrange or group the orthogonal plots for the analyzed plurality of samples to form a first across-sample plot, as shown in FIG. 7, wherein the first across-sample plot is configured so as to have a retention time axis 230 and a sample indicia axis 240, and to include a graphical representation of the orthogonal plots across the plurality of samples, arranged by sample indicia. That is, the orthogonal plots are arranged along the sample indicia axis such that the orthogonal plots are adjacently disposed over the same retention time range of the retention time axis associated with the selected intensity peak or intensity peak arrangement 225, such that the appearance (or absence) of the selected intensity peak or intensity peak arrangement may be analyzed concurrently across any or all of the plurality of samples.

In performing the across-sample analysis, it may be beneficial in some instances, to have expedient access to other information associated with any of the orthogonal plots for the selected intensity peak or intensity peak arrangement of the plurality of samples. As such, in some aspects, the processor device 130 may further be configured to execute instructions/computer readable program code portions so as to provide the capability to selectively toggle between the orthogonal plot and the profile plot of the intensity peak or the intensity peak arrangement of at least one of the samples (see, e.g., FIG. 10). That is, for example, if the across-sample plot (i.e., orthogonal plots for a plurality of the samples) is displayed on a display 150, selecting one of the orthogonal plots corresponding to one of the sample, for instance, by mouse or cursor selection, may cause the across-sample plot to be replaced on the display by the corresponding profile plot of the selected orthogonal plot corresponding thereto. In other instances, the corresponding profile plot 800 may be displayed on the display 150 concurrently with and adjacent to the across-sample plot (i.e., as in inset or in a designated portion of the display 150). That is, in some cases, the analysis method may also comprise concurrently displaying the profile plot and the orthogonal plot of the well-separated ion peak or the ion peak arrangement of at least one of the samples. In further instances, similar to the selection of the one of the orthogonal plots to display the profile plot, the profile plot may be further deselected, for example, by mouse or cursor selection, which may then cause the profile plot to be removed from the display. The display would thus return to the across-sample plot.

In particular aspects of the present disclosure, the across-sample analysis may be implemented in different manners as will be appreciated by one skilled in the art. For example, since some aspects of the present disclosure involve determining characteristics of the selected intensity peak or intensity peak arrangement in relation to the profile plot thereof for each sample, the processor device 130 may further be configured to execute instructions/computer readable program code portions so as to superimpose the profile plots of the selected ion for at least a portion of the samples upon each other so as to form a second across-sample plot (see, e.g., element 900 in FIG. 11, showing only three superimposed profile plots for the sake of clarity). In such instances, the second across-sample plot 900 may be characterized as viewing the first across-sample plot (i.e., sample indicia versus retention time for the orthogonal plots) from the x-axis (time retention axis) in a direction along the y-axis (sample indicia axis). For example, such a view may be characterized as a view from along the x-axis in the increasing direction of the y-axis, from y=0, or a view of the x-axis in the decreasing direction of the y-axis, from y>0. Such a view may provide particular information from the across-sample analysis, for example, whether the characteristic intensity of a particular peak of a particular sample is of a greater than expected magnitude given the relative amount of that ion or ion component in the other samples. In still further aspects, the processor device 130 may further be configured to execute instructions/computer readable program code portions so as to display the second across-sample plot on a display 150, for example, by toggling the second across-sample plot with the first across-sample plot having the retention time axis and a sample indicia axis, and including a graphical representation of the orthogonal plots across the plurality of samples, by way of mouse or cursor selection. In other instances, the second across-sample plot may be displayed concurrently with the first across-sample plot, for example, as in inset or in a designated portion of the display, also by way of mouse or cursor selection.

Aspects of the present disclosure also provide methods of analyzing metabolomics data, as shown generally in the operational flow diagram of FIG. 8, and as previously discussed herein. In addition to providing appropriate apparatuses and methods, aspects of the present disclosure may also provide associated computer program products for performing the functions/operations/steps disclosed above, in the form of, for example, a computer-readable storage medium (i.e., memory device 140) having particular computer-readable program code portions stored therein by the medium that, in response to execution by the processor device 130, cause the apparatus to at least perform the steps disclosed herein. In this regard, FIG. 8 is an operational flow diagram associated with particular methods, apparatuses and computer program products according to particular aspects of the present disclosure. It will be understood that each block or step of the operational flow diagram or combinations of blocks in the operational flow diagram can be implemented by appropriate computer program instructions executed by the processor device 130. These computer program instructions may be loaded onto a computer device or other programmable apparatus for executing the functions specified in the operational flow diagram otherwise associated with the method(s) disclosed herein. These computer program instructions may also be stored in a computer-readable memory (i.e., memory device 140), so as to be accessible by a computer device or other programmable apparatus in a particular manner, such that the executable instructions stored in the computer-readable memory may produce or facilitate the operation of an article of manufacture capable of directing or otherwise executing the instructions which implement the functions specified in the operational flow diagram otherwise associated with the method(s) disclosed herein. The computer program instructions may also be loaded onto a computer device or other programmable apparatus to cause a series of operational steps to be performed on the computer device or other programmable apparatus to produce a computer-implemented process such that the instructions executed by the computer device or other programmable apparatus provide or otherwise direct appropriate steps for implementing the functions/steps specified in the operational flow diagram otherwise associated with the method(s) disclosed herein. It will also be understood that each step of the operational flow diagram, or combinations of steps in the operational flow diagram, can be implemented by special purpose hardware-based computer systems which perform the specified functions or steps, or combinations of special purpose hardware and computer instructions (software).

Many modifications and other aspects of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method of analyzing data for a plurality of samples obtained from a component separation and mass spectrometer system, the data including a data set for each sample, each data set including sample indicia, sample ion mass, retention time, and intensity, said method comprising:
forming a profile plot for each sample from the data obtained from the component separation and mass spectrometer system and corresponding to the respective sample, each profile plot having a retention time axis and an intensity axis, and including a graphical representation of intensity as a function of retention time for a selected sample ion mass;
identifying an intensity peak arrangement corresponding to a selected ion in the profile plot for each sample, the intensity peak arrangement including at least one identifying peak, each of the at least one identifying peak having a peak range and a characteristic intensity within the peak range;
forming an orthogonal plot, corresponding to the profile plot for the selected sample ion mass, for each sample, the orthogonal plot extending along the retention time axis in a plane perpendicular to the intensity axis;
forming a first across-sample plot from the orthogonal plots of the plurality of samples, the first across-sample plot having the retention time axis and a sample indicia axis, and including a graphical representation of the orthogonal plots across the plurality of samples; and
representing the characteristic intensity of each of the at least one identifying peak on the retention time axis of the orthogonal plot for each sample, with gradated indicia having an expression for each of the at least one identifying peak in proportion to a relation of the characteristic intensity to a defined range, across the plurality of samples.

2. The method according to claim 1, wherein the at least one identifying peak includes a main peak and at least one sub-peak, and wherein representing the characteristic intensity of each of the at least one identifying peak further comprises representing the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

3. The method according to claim 1, comprising representing the peak range of each of the at least one identifying peak on the orthogonal plot with range indicia, the range indicia having a first indicium representing an initiation of the peak range and a second indicium representing a termination of the peak range, for each of the at least identifying peak.

4. The method according to claim 3, wherein the at least one identifying peak includes a main peak and at least one sub-peak, and wherein representing the peak range of each of the at least one identifying peak on the orthogonal plot with range indicia, comprises representing the peak range of each of the at least one identifying peak on the orthogonal plot with range indicia, with the second indicium of the range indicia of the main peak also representing the first indicium of the range indicia of a next sub-peak of the intensity peak arrangement, the next sub-peak being one of a shoulder peak and a secondary peak associated with the main peak.

5. The method according to claim 3, wherein the at least one identifying peak includes a main peak and at least one sub-peak, and wherein representing the peak range of each of the at least one identifying peak on the orthogonal plot with range indicia, comprises representing the peak range of each of the at least one identifying peak on the orthogonal plot with range indicia, with the second indicium of the range indicia of one of the sub-peaks also representing the first indicium of the range indicia of a next sub-peak of the intensity peak arrangement, the next sub-peak being one of a shoulder peak and a secondary peak associated with the one of the sub-peaks.

6. The method according to claim 1, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

7. The method according to claim 1, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

8. The method according to claim 1, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

9. The method according to claim 1, wherein the at least one identifying peak includes a main peak and at least one sub-peak, and wherein representing the characteristic intensity of each of the at least one identifying peak on the retention time axis of the orthogonal plot, comprises representing the characteristic intensity of each of the at least one identifying peak on the retention time axis of the orthogonal plot with different shapes, including a first shape for the characteristic intensity of the main peak and a second shape for the characteristic intensity of one of the at least one sub-peak.

10. The method according to claim 1, comprising determining an area associated with any of the at least one identifying peak of the intensity peak arrangement for the selected ion, using an integration procedure, the determined area being associated with a relative quantity of an ion component corresponding thereto in the respective sample.

11. The method according to claim 10, comprising determining an identity peak for the selected ion from the at least one identifying peak, wherein determining an area comprises determining an area associated with the identity peak for the selected ion, using an integration procedure, the determined area of the identity peak being associated with a relative quantity of the selected ion corresponding thereto in the respective sample.

12. The method according to claim 1, comprising selectively toggling between the profile plot and the orthogonal plot of the intensity peak arrangement of at least one of the samples.

13. The method according to claim 1, comprising concurrently displaying the profile plot and the orthogonal plot of the ion peak arrangement of at least one of the samples.

14. The method according to claim 1, comprising superimposing the profile plots of the selected ion for at least a portion of the samples on a second across-sample plot.

15. The method according to claim 14, comprising forming a first across-sample plot from the orthogonal plots of the plurality of samples, the first across-sample plot having the retention time axis and a sample indicia axis, and including a graphical representation of the orthogonal plots across the plurality of samples, and displaying the second across-sample plot concurrently with the first across-sample plot.

16. An apparatus for analyzing data for a plurality of samples obtained from a component separation and mass spectrometer system, the data including a data set for each sample, each data set including sample indicia, sample ion mass, retention time, and intensity, the apparatus comprising a processor or processing circuitry and a memory storing computer-readable program code or executable instructions that, in response to execution by the processor or processing circuitry, cause the apparatus to at least:
form a profile plot for each sample from the data obtained from the component separation and mass spectrometer system and corresponding to the respective sample, each profile plot having a retention time axis and an intensity axis, and including a graphical representation of intensity as a function of retention time for a selected sample ion mass;
identify an intensity peak arrangement corresponding to a selected ion in the profile plot for each sample, the intensity peak arrangement including at least one identifying peak, each of the at least one identifying peak having a peak range and a characteristic intensity within the peak range;
form an orthogonal plot, corresponding to the profile plot for the selected sample ion mass, for each sample, the orthogonal plot extending along the retention time axis in a plane perpendicular to the intensity axis;
form a first across-sample plot from the orthogonal plots of the plurality of samples, the first across-sample plot having the retention time axis and a sample indicia axis, and including a graphical representation of the orthogonal plots across the plurality of samples; and represent the characteristic intensity of each of the at least one identifying peak on the retention time axis of the orthogonal plot for each sample, with gradated indicia having an expression for each of the at least one identifying peak in proportion to a relation of the characteristic intensity to a defined range, across the plurality of samples.

17. The apparatus according to claim 16, wherein the at least one identifying peak includes a main peak and at least one sub-peak, and wherein the apparatus is further caused to represent the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

18. The apparatus according to claim 16, wherein the memory stores further computer-readable program code or executable instructions that, in response to execution by the processing circuitry, cause the apparatus to further represent the peak range of each of the at least one identifying peak on the orthogonal plot with range indicia, the range indicia having a first indicium representing an initiation of the peak range and a second indicium representing a termination of the peak range, for each of the at least identifying peak.

19. The apparatus according to claim 18, wherein the at least one identifying peak includes a main peak and at least one sub-peak, and wherein the apparatus is further caused to represent the peak range of each of the at least one identifying peak on the orthogonal plot with range indicia, with the second indicium of the range indicia of the main peak also representing the first indicium of the range indicia of a next sub-peak of the intensity peak arrangement, the next sub-peak being one of a shoulder peak and a secondary peak associated with the main peak.

20. The apparatus according to claim 18, wherein the at least one identifying peak includes a main peak and at least one sub-peak, and wherein the apparatus is further caused to represent the peak range of each of the at least one identifying peak on the orthogonal plot with range indicia, with the second indicium of the range indicia of one of the sub-peaks also representing the first indicium of the range indicia of a next sub-peak of the intensity peak arrangement, the next sub-peak being one of a shoulder peak and a secondary peak associated with the one of the sub-peaks.

21. The apparatus according to claim 16, wherein the at least one identifying peak includes a main peak and at least one sub-peak, and wherein the apparatus is further caused to represent the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

22. The apparatus according to claim 16, wherein the at least one identifying peak includes a main peak and at least one sub-peak, and wherein the apparatus is further caused to represent the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

23. The apparatus according to claim 16, wherein the at least one identifying peak includes a main peak and at least one sub-peak, and wherein the apparatus is further caused to represent the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

24. The apparatus according to claim 16, wherein the at least one identifying peak includes a main peak and at least one sub-peak, and wherein the apparatus is further caused to represent the characteristic intensity of each of the at least one identifying peak on the retention time axis of the orthogonal plot with different shapes, including a first shape for the characteristic intensity of the main peak and a second shape for the characteristic intensity of one of the at least one sub-peak.

25. The apparatus according to claim 16, wherein the memory stores further computer-readable program code or executable instructions that, in response to execution by the processing circuitry, cause the apparatus to further determine an area associated with any of the at least one identifying peak of the intensity peak arrangement for the selected ion, using an integration procedure, the determined area being associated with a relative quantity of an ion component corresponding thereto in the respective sample.

26. The apparatus according to claim 25, wherein the memory stores further computer-readable program code or executable instructions that, in response to execution by the processing circuitry, cause the apparatus to further determine an identity peak for the selected ion from the at least one identifying peak, wherein determining an area comprises determining an area associated with the identity peak for the selected ion, using an integration procedure, the determined area of the identity peak being associated with a relative quantity of the selected ion corresponding thereto in the respective sample.

27. The apparatus according to claim 16, wherein the memory stores further computer-readable program code or executable instructions that, in response to execution by the processing circuitry, cause the apparatus to further selectively toggle between the profile plot and the orthogonal plot of the intensity peak arrangement of at least one of the samples.

28. The apparatus according to claim 16, wherein the memory stores further computer-readable program code or executable instructions that, in response to execution by the processing circuitry, cause the apparatus to further concurrently display the profile plot and the orthogonal plot of the ion peak arrangement of at least one of the samples.

29. The apparatus according to claim 16, wherein the memory stores further computer-readable program code or executable instructions that, in response to execution by the processing circuitry, cause the apparatus to further superimpose the profile plots of the selected ion for at least a portion of the samples on a second across-sample plot.

30. The apparatus according to claim 28, wherein the memory stores further computer-readable program code or executable instructions that, in response to execution by the processing circuitry, cause the apparatus to further form a first across-sample plot from the orthogonal plots of the plurality of samples, the first across-sample plot having the retention time axis and a sample indicia axis, and including a graphical representation of the orthogonal plots across the plurality of samples, and displaying the second across-sample plot concurrently with the first across-sample plot.

31. A non-transitory computer-readable storage medium having computer-readable program code stored therein for analyzing data for a plurality of samples obtained from a component separation and mass spectrometer system, the data including a data set for each sample, each data set including sample indicia, sample ion mass, retention time, and intensity, the computer-readable program code, in response to execution by a processor or processing circuitry, causing an apparatus to at least:
  form a profile plot for each sample from the data obtained from the component separation and mass spectrometer system and corresponding to the respective sample, each profile plot having a retention time axis and an intensity axis, and including a graphical representation of intensity as a function of retention time for a selected sample ion mass;
  identify an intensity peak arrangement corresponding to a selected ion in the profile plot for each sample, the intensity peak arrangement including at least one identifying peak, each of the at least one identifying peak having a peak range and a characteristic intensity within the peak range;
  form an orthogonal plot, corresponding to the profile plot for the selected sample ion mass, for each sample, the orthogonal plot extending along the retention time axis in a plane perpendicular to the intensity axis;
  form a first across-sample plot from the orthogonal plots of the plurality of samples, the first across-sample plot having the retention time axis and a sample indicia axis, and including a graphical representation of the orthogonal plots across the plurality of samples; and
  represent the characteristic intensity of each of the at least one identifying peak on the retention time axis of the orthogonal plot for each sample, with gradated indicia having an expression for each of the at least one identifying peak in proportion to a relation of the characteristic intensity to a defined range, across the plurality of samples.

32. The computer-readable storage medium according to claim 31, wherein the at least one identifying peak includes a main peak and at least one sub-peak, and wherein further computer-readable program code stored in the computer-readable storage medium, in response to execution by the processor or processing circuitry, causes the apparatus to further represent the characteristic intensity of the at least one identifying peak on the retention time axis of the orthogonal plot with gradated indicia having a maximum expression for the characteristic intensity of the main peak and a lesser expression for the characteristic intensity of each of the at least one sub-peak.

33. The computer-readable storage medium according to claim 31, wherein further computer-readable program code stored in the computer-readable storage medium, in response to execution by the processor or processing circuitry, causes the apparatus to further represent the peak range of each of the at least one identifying peak on the orthogonal plot with range indicia, the range indicia having a first indicium representing an initiation of the peak range and a second indicium representing a termination of the peak range, for each of the at least identifying peak.

34. The computer-readable storage medium according to claim 33, wherein the at least one identifying peak includes a main peak and at least one sub-peak, and further computer-readable program code stored in the computer-readable storage medium, in response to execution by the processor or processing circuitry, causes the apparatus to further represent the peak range of each of the at least one identifying peak on the orthogonal plot with range indicia, with the second indicium of the range indicia of the main peak also representing the first indicium of the range indicia of a next sub-peak of the intensity peak arrangement, the next sub-peak being one of a shoulder peak and a secondary peak associated with the main peak.

35. The computer-readable storage medium according to claim 33, wherein the at least one identifying peak includes a main peak and at least one sub-peak, and further computer-readable program code stored in the computer-readable storage medium, in response to execution by the processor or processing circuitry, causes the apparatus to further represent the peak range of each of the at least one identifying peak on the orthogonal plot with range indicia, with the second indicium of the range indicia of one of the sub-peaks also representing the first indicium of the range indicia of a next sub-peak of the intensity peak arrangement, the next sub-peak being one of a shoulder peak and a secondary peak associated with the one of the sub-peaks.

36. The computer-readable storage medium according to claim 31, wherein the at least one identifying peak includes a main peak and at least one sub-peak, and further computer-readable program code stored in the computer-readable storage medium, in response to execution by the processor or processing circuitry, causes the apparatus to further represent the characteristic intensity of each of the at least one identifying peak on the retention time axis of the orthogonal plot with a gradated shape having a maximum size of the shape for the characteristic intensity of the main peak and a lesser size of the shape for the characteristic intensity of each of the at least one sub-peak.

37. The computer-readable storage medium according to claim 31, wherein the at least one identifying peak includes a main peak and at least one sub-peak, and further computer-readable program code stored in the computer-readable storage medium, in response to execution by the processor or processing circuitry, causes the apparatus to further represent the characteristic intensity of each of the at least one identifying peak on the retention time axis of the orthogonal plot with a gradated shading having a maximum intensity of the shading for the characteristic intensity of the main peak and a lesser intensity of the shading for the characteristic intensity of each of the at least one sub-peak.

38. The computer-readable storage medium according to claim 31, wherein the at least one identifying peak includes a main peak and at least one sub-peak, and further computer-readable program code stored in the computer-readable storage medium, in response to execution by the processor or processing circuitry, causes the apparatus to further represent the characteristic intensity of each of the at least one identifying peak on the retention time axis of the orthogonal plot with a gradated color having a maximum intensity of the color for the characteristic intensity of the main peak and a lesser intensity of the color for the characteristic intensity of each of the at least one sub-peak.

39. The computer-readable storage medium according to claim 31, wherein the at least one identifying peak includes a main peak and at least one sub-peak, and further computer-readable program code stored in the computer-readable storage medium, in response to execution by the processor or processing circuitry, causes the apparatus to further represent the characteristic intensity of each of the at least one identifying peak on the retention time axis of the orthogonal plot with different shapes, including a first shape for the characteristic intensity of the main peak and a second shape for the characteristic intensity of one of the at least one sub-peak.

40. The computer-readable storage medium according to claim 31, wherein further computer-readable program code stored in the computer-readable storage medium, in response to execution by the processor or processing circuitry, causes the apparatus to further determine an area associated with any of the at least one identifying peak of the intensity peak arrangement for the selected ion, using an integration procedure, the determined area being associated with a relative quantity of an ion component corresponding thereto in the respective sample.

41. The computer-readable storage medium according to claim 40, wherein further computer-readable program code stored in the computer-readable storage medium, in response to execution by the processor or processing circuitry, causes the apparatus to further determine an identity peak for the selected ion from the at least one identifying peak, wherein determining an area comprises determining an area associated with the identity peak for the selected ion, using an integration procedure, the determined area of the identity peak being associated with a relative quantity of the selected ion corresponding thereto in the respective sample.

42. The computer-readable storage medium according to claim 31, wherein further computer-readable program code stored in the computer-readable storage medium, in response to execution by the processor or processing circuitry, causes the apparatus to further selectively toggle between the profile plot and the orthogonal plot of the intensity peak arrangement of at least one of the samples.

43. The computer-readable storage medium according to claim 31, wherein further computer-readable program code stored in the computer-readable storage medium, in response to execution by the processor or processing circuitry, causes the apparatus to further concurrently display the profile plot and the orthogonal plot of the ion peak arrangement of at least one of the samples.

44. The computer-readable storage medium according to claim 31, wherein further computer-readable program code stored in the computer-readable storage medium, in response to execution by the processor or processing circuitry, causes the apparatus to further superimpose the profile plots of the selected ion for at least a portion of the samples on a second across-sample plot.

45. The computer-readable storage medium according to claim 43, wherein further computer-readable program code stored in the computer-readable storage medium, in response to execution by the processor or processing circuitry, causes the apparatus to further form a first across-sample plot from the orthogonal plots of the plurality of samples, the first across-sample plot having the retention time axis and a sample indicia axis, and including a graphical representation of the orthogonal plots across the plurality of samples, and displaying the second across-sample plot concurrently with the first across-sample plot.

* * * * *